United States Patent
Sankovsky

(10) Patent No.: US 12,056,170 B2
(45) Date of Patent: *Aug. 6, 2024

(54) PROCESSING SYSTEM HAVING MACHINE LEARNING ENGINE FOR PROVIDING CUSTOMIZED USER FUNCTIONS

(71) Applicant: ALLSTATE INSURANCE COMPANY, Northbrook, IL (US)

(72) Inventor: Jenny Sankovsky, Hawthorn Woods, IL (US)

(73) Assignee: ALLSTATE INSURANCE COMPANY, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/729,436

(22) Filed: Apr. 26, 2022

(65) Prior Publication Data

US 2023/0077953 A1 Mar. 16, 2023

Related U.S. Application Data

(63) Continuation of application No. 15/653,641, filed on Jul. 19, 2017, now Pat. No. 11,314,798.

(51) Int. Cl.
*G06F 16/34* (2019.01)
*A61B 5/00* (2006.01)
(Continued)

(52) U.S. Cl.
CPC .......... *G06F 16/345* (2019.01); *A61B 5/7267* (2013.01); *G06F 16/335* (2019.01);
(Continued)

(58) Field of Classification Search
None
See application file for complete search history.

(56) References Cited

U.S. PATENT DOCUMENTS

| 4,827,458 A | 5/1989 | D'Alayer de Costemore D'Arc |
| 6,389,447 B1 | 5/2002 | Singh |

(Continued)

FOREIGN PATENT DOCUMENTS

| WO | WO-2014145956 A1 | 9/2014 |
| WO | WO-2015131242 A1 | 9/2015 |

(Continued)

OTHER PUBLICATIONS

Mar. 8, 2021—(CA) Office Action—Application No. 3,070,422 (006591.02379), 6 Pages.

(Continued)

*Primary Examiner* — Daniel C Puentes
(74) *Attorney, Agent, or Firm* — Polsinelli PC

(57) ABSTRACT

Systems and apparatuses for generating customized user output are provided. The system may collect sensor data, associated with the user, from a variety of sources. The system may use the sensor data to generate a customized user output. The system may analyze the sensor data, and determine, based on the sensor data and the customized user output, one or more user recommendation outputs. The system may update the customized user output based on additional or subsequent sensor data, and/or based on whether or not the user recommendation output was completed, as determined from subsequent sensor data.

20 Claims, 12 Drawing Sheets

| Health Output 610 | Transportation Output 620 | Security Output 630 |
|---|---|---|
| Normal blood pressure +5 | No car accidents +7 | No home security system -3 |
| Low cholesterol +7 | Bought a new car +5 | Live in high crime area -9 |
| Low heart rate +3 | | |
| Normal weight +8 | | |
| Runs 3x per week +10 | | |
| Total = 33 | Total = 12 | Total = -12 |

640
Customized User Output = (33 + 12 − 12) / 3 = 11

(51) Int. Cl.
*G06F 16/335* (2019.01)
*G06F 16/9535* (2019.01)
*A61B 5/024* (2006.01)
*G06F 16/435* (2019.01)
*G06N 20/00* (2019.01)

(52) U.S. Cl.
CPC ........ *G06F 16/9535* (2019.01); *A61B 5/0022* (2013.01); *A61B 5/024* (2013.01); *A61B 5/4848* (2013.01); *A61B 5/4884* (2013.01); *A61B 5/746* (2013.01); *A61B 2503/12* (2013.01); *G06F 16/437* (2019.01); *G06N 20/00* (2019.01)

(56) References Cited

U.S. PATENT DOCUMENTS

| | | | |
|---|---|---|---|
| 8,358,214 | B2 | 1/2013 | Amigo et al. |
| 8,519,860 | B2 | 8/2013 | Johnson et al. |
| 8,566,121 | B2 | 10/2013 | Ramasubramanian et al. |
| 8,751,636 | B2 | 6/2014 | Tseng et al. |
| 9,129,219 | B1 | 9/2015 | Robertson et al. |
| 9,299,241 | B1 | 3/2016 | Monical et al. |
| 9,398,854 | B2 | 7/2016 | Proud |
| 9,549,393 | B2 | 1/2017 | Bendeck et al. |
| 9,712,509 | B1 | 7/2017 | Marshall et al. |
| 11,314,798 | B2 * | 4/2022 | Sankovsky ............ G16H 50/30 |
| 2008/0189142 | A1 | 8/2008 | Brown et al. |
| 2010/0228584 | A1 | 9/2010 | Nash |
| 2011/0161119 | A1 | 6/2011 | Collins |
| 2011/0213628 | A1 | 9/2011 | Peak et al. |
| 2014/0279074 | A1 | 9/2014 | Chen et al. |
| 2015/0161719 | A1 | 6/2015 | Abhyanker |
| 2015/0261769 | A1 | 9/2015 | Ono et al. |
| 2015/0269848 | A1 * | 9/2015 | Yuen ...................... A61B 5/222 434/236 |
| 2016/0098530 | A1 | 4/2016 | Dill et al. |
| 2016/0217532 | A1 | 7/2016 | Slavin |
| 2017/0069034 | A1 * | 3/2017 | Luciani .................. H04W 4/90 |
| 2023/0154332 | A1 * | 5/2023 | Nayak .............. G08G 1/096716 701/301 |

FOREIGN PATENT DOCUMENTS

| | | |
|---|---|---|
| WO | WO-2016028228 A1 | 2/2016 |
| WO | WO-2016028933 A1 | 2/2016 |
| WO | WO-2016097376 A1 | 6/2016 |
| WO | WO-2016151061 A1 | 9/2016 |

OTHER PUBLICATIONS

Extended European Search Report for European Application No. 18835210.8 dated Mar. 15, 2021, 12 pages.

International Search report and Written Opinion for International Application No. PCT/US2018/042661, mailed Sep. 27, 2018, 9 pages.

Olson P., "Wearable Tech Is Plugging Into Health Insurance", Retrieved from URL: https://www.forbes.com/sites/parmyolson/2014/06/19/wearable-tech-health-insurance/#112972e518bd, on Jun. 19, 2014, 7 pages.

Patel S., et al., "A Review of Wearable Sensors and Systems with Application in Rehabilitation," Journal of NeuroEngineering and Rehabilitation, 2012, Apr. 20, 2012, vol. 9 (21), Retrieved from URL: https://www.jneuroengrehab.biomedcentral.com/articles/10.1186/1743-0003-9-21, pp. 1-17.

* cited by examiner

| Health Output (610) | Transportation Output (620) | Security Output (630) |
|---|---|---|
| Normal blood pressure +5 | No car accidents +7 | No home security system -3 |
| Low cholesterol +7 | Bought a new car +5 | Live in high crime area -9 |
| Low heart rate +3 | | |
| Normal weight +8 | | |
| Runs 3x per week +10 | | |
| Total = 33 | Total = 12 | Total = -12 |

Customized User Output = (33 + 12 – 12) / 3 = 11 (640)

FIG. 6

PROCESSING SYSTEM HAVING MACHINE LEARNING ENGINE FOR PROVIDING CUSTOMIZED USER FUNCTIONS

CROSS-REFERENCE TO RELATED APPLICATIONS

The present application claims priority to U.S. patent application Ser. No. 15/653,641 filed on Jul. 19, 2017, which is incorporated by reference in its entirety herein.

FIELD OF ART

Aspects of the disclosure relate to processing systems. In particular, aspects of the disclosure related to processing systems having a machine learning engine and machine learning datasets to generate customized user outputs.

BACKGROUND

Users interact with computing devices in a variety of ways. For example, users interact with cell phones, personal computers, fitness trackers, tablets, and the like. Each interaction yields sensor data, associated with characteristics of a user, that may be used to generate outputs unique to the user. Users might not be aware of how best to protect themselves based on the totality of their lifestyle. Accordingly, it would be advantageous to aggregate this sensor data to generate customized outputs for the user to effectively protect users.

SUMMARY

In light of the foregoing background, the following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects of the disclosure related to evaluating user habits/characteristics based on sensor data received from one or more devices. In some examples, sensor data may include health sensor data, transportation sensor data, social sensor data, home sensor data, security sensor data, financial sensor data, and other miscellaneous sensor data. The sensor data may be analyzed and aggregated to generate a determination and provide an output to a user. In some examples, machine learning may be used to generate one or more determinations and/or one or more outputs.

When new, updated, or additional sensor data is received, a server may generate a recommendation output. The recommendation output may be transmitted to a computing device (cell phone, laptop, and the like) associated with the user by way of a message (text message, email, and the like). Additional data may be received which may be analyzed by the server to determine whether the recommendation output was implemented or completed. Based on a determination that the recommendation output was completed, the server may transmit, to a device associated with the user, a positive benefit or incentive. If it is determined that the recommendation output was not completed or implemented, the server may transmit, to a device associated with the user, a negative benefit. The positive benefit and the negative benefit may comprise recommended products for the user. The sensor data indicating whether the recommendation output was completed or implemented may affect a customized user output.

The customized user output may be updated as new sensor data is received and the user may receive additional benefits (e.g., positive or negative) which may correspond with changes in the customized user output.

The arrangements described may also include other additional elements, steps, computer-executable instructions, or computer-readable data structures. In this regard, other embodiments are disclosed and claimed herein as well. The details of these and other embodiments of the present invention are set forth in the accompanying drawings and the description below. Other features and advantages of the invention will be apparent from the description, drawings, and claims.

BRIEF DESCRIPTION OF THE DRAWINGS

The present invention is illustrated by way of example and is not limited by the accompanying figures in which like reference numerals indicate similar elements and in which:

FIG. 6 shows an example calculation of a customized user output in accordance with one or more aspects described herein.

DETAILED DESCRIPTION

Figure 1:
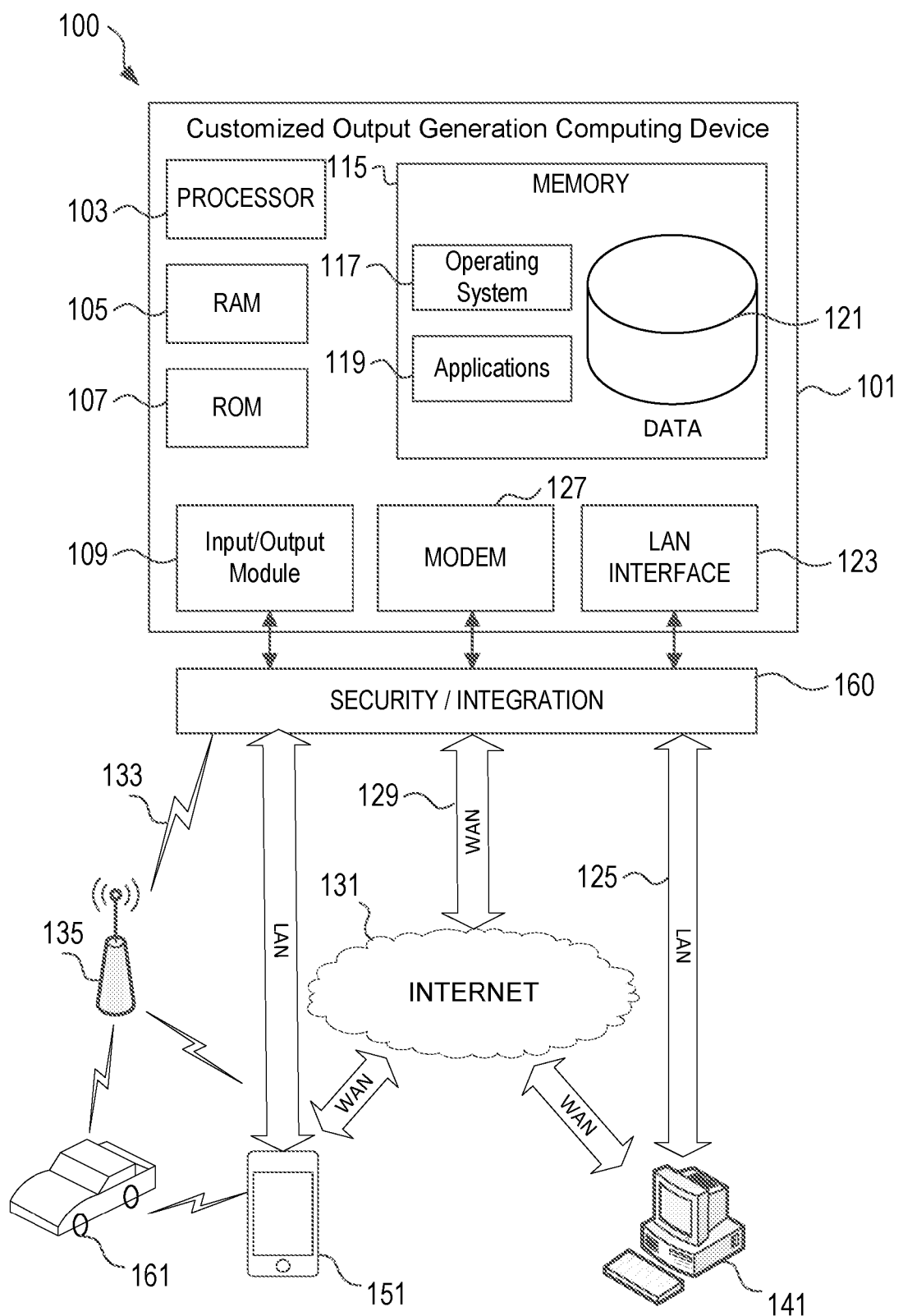
FIG. 1 shows a block diagram of one example customized output generation computing device (or system) in a computer system that may be used according to one or more illustrative embodiments of the disclosure.

In the following description of the various embodiments, reference is made to the accompanying drawings, which form a part hereof, and in which is shown by way of illustration, various embodiments of the disclosure that may be practiced. It is to be understood that other embodiments may be utilized.

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more computer-readable storage media having computer-readable program code, or instructions, embodied in or on the storage media. Any suitable computer-readable storage media may be utilized, including hard disks, CD-ROMs, optical storage devices, magnetic storage devices, and/or any combination thereof. In addition, various signals representing sensor data or events as described herein may be transferred between a source and a destination in the form of electromagnetic waves traveling through signal-conducting media such as metal wires, optical fibers, and/or wireless transmission media (e.g., air and/or space).

As will be discussed more fully herein, arrangements described herein are directed to determining, based on sensor data received from a plurality of devices associated with a user, a customized user output. The customized user output may in fact be a numeric output or it may be a collection of sensor data all of which may be compared and weighed to determine characteristics/interests of the user. The customized user output may be an absolute value, or may be a relative value as compared to a group. This group may be selected by the user and/or defined by a server. For example, the server may select the group based on a zip code, a geographic region, user interests, and the like. The customized user output may be used to provide user recommendation output to the user, and to determine a dynamic product offering such as benefits for the user. For example, if the customized user output is below a predetermined threshold, protection products may be offered to the user. If the customized user output is above a predetermined threshold, prevention products may be offered to the user. The customized user output may be updated at predetermined intervals, or when new sensor data is received.

The customized user output may be determined using machine learning. Machine learning datasets may be generated based on sensor data associated with a particular user and additional sensor data associated with a plurality of users. The users may include different characteristics, and a server may identify, based on one or more characteristics of the user, a machine learning dataset. The server may compare the characteristics of the user to the machine learning dataset to generate the customized user output.

In an example, a user may reserve a temporary residence (e.g., a travel booking). A server may receive sensor data associated with the temporary residence such as location, cost, user ratings and reviews, crime statistics, age, recent property damage, and the like. This sensor data may contribute to the user's customized user output. The server may use this sensor data and the customized user output to generate a recommended action, such as "lock up valuables when you leave." The server may then receive an indication of whether the recommended action was completed. If so, the server may generate one or more positive benefits to provide to the user. If the server does not receive an indication that the recommended action was completed, or receives an indication that it was not completed, the server may generate one or more negative benefits to provide to the user. Furthermore, based on the customized user output and the sensor data, the server may generate an offer for additional products. The server may transmit the offer for additional products regardless of whether the user recommendation output was implemented.

In another example, a server may use sensor data associated with the user's calendar, heart rate, blood pressure, tone, language, and the like to determine that the user may be experiencing a high stress level. This sensor data may contribute to the user's customized user output. The server may use this sensor data and the customized user output to generate one or more recommendation output, such as "listen to soothing jazz music." The server may then receive an indication of whether the recommendation output was implemented (e.g., based on sensor data indicating a type of music to which the user listened in a predetermined or designated time period after generation of the recommendation output. If the recommendation output was implemented, the server may generate one or more positive benefits to provide to the user. If the server does not receive an indication that the recommendation output was implemented, the server may generate one or more negative benefits to provide to the user. Furthermore, based on the customized user output and the sensor data, the server may transmit an offer for additional products. The server may transmit the offer for additional products regardless of whether the user recommendation output was implemented.

In another example, a user may be walking in a neighborhood identified by the system as having a crime rate above a predetermined threshold. A server may receive sensor data such as location, time, height/weight/age/gender of the user, crime statistics for the neighborhood, crime statistics for surrounding neighborhood, and the like. This sensor data may contribute to the user's customized user output. The server may use this sensor data and the customized user output to generate a recommendation output, such as "do not walk alone in this area at night with headphones in." The server may receive an indication of whether the generated recommendation output was implemented (e.g., based on sensors indicating a position of headphones, or the like). If the generated recommendation was implemented, the server may generate one or more positive benefits to provide to the user. If the recommendation output was not implemented, the server may generate one or more negative benefits for the user. Furthermore, based on the customized user output and the sensor data, the server may transmit an offer for additional products. The server may transmit the offer for additional products regardless of whether the user recommendation output was implemented.

These and various other arrangements will be described more fully herein.

FIG. 1 shows a block diagram of one example customized output generation computing device (or system) in a computer system 100 that may be used according to one or more illustrative embodiments of the disclosure. The customized output generation computing device 101 may have a processor 103 for controlling overall operation of the customized output generation computing device 101 and its associated components, including Random Access Memory (RAM) 105, Read Only Memory (ROM) 107, input/output module 109, and memory 115. The customized output generation computing device 101, along with one or more additional devices (e.g., terminals 141 and 151, security and integration hardware 160) may correspond to any of multiple systems or devices described herein, such as personal mobile devices, insurance systems servers, internal data sources, external data sources and other various devices. These various computing systems may be configured individually or in combination, as described herein, for receiving signals and/or transmissions from one or more computing devices.

Input/Output (I/O) 109 may include a microphone, keypad, touch screen, and/or stylus through which a user of the customized output generation computing device 101 may provide input, and may also include one or more of a speaker for providing audio output and a video display device for providing textual, audiovisual and/or graphical output. Software may be stored within memory 115 and/or storage to provide instructions to processor 103 for enabling the customized output generation computing device 101 to perform various actions. For example, memory 115 may store software used by the customized output generation computing device 101, such as an operating system 117, application programs 119, and an associated internal database 121. The various hardware memory units in memory 115 may include volatile and nonvolatile, removable and non-removable media implemented in any method or technology for storage of information such as computer-readable instructions, data structures, program modules or other data. Certain devices and systems may have minimum hardware requirements in order to support sufficient storage capacity, processing capacity, analysis capacity, network communication, etc. For instance, in some embodiments, one or more nonvolatile hardware memory units having a minimum size (e.g., at least 1 gigabyte (GB), 2 GB, 5 GB, etc.), and/or one or more volatile hardware memory units having a minimum size (e.g., 256 megabytes (MB), 512 MB, 1 GB, etc.) may be used in a customized output generation computing device 101 (e.g., a personal mobile device, etc.), in order to receive and analyze the signals, transmissions, etc. Memory 115 also may include one or more physical persistent memory devices and/or one or more non-persistent memory devices. Memory 115 may include, but is not limited to, random access memory (RAM) 105, read only memory (ROM) 107, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 103.

Processor 103 may include a single central processing unit (CPU), which may be a single-core or multi-core processor (e.g., dual-core, quad-core, etc.), or may include multiple CPUs. Processor(s) 103 may have various bit sizes (e.g., 16-bit, 32-bit, 64-bit, 96-bit, 128-bit, etc.) and various processor speeds (ranging from 100 MHz to 5 Ghz or faster). Processor(s) 103 and its associated components may allow the customized output generation computing device 101 to execute a series of computer-readable instructions, for example, receive sensor data associated with a user, generate a customized user output, and offer user recommendation outputs, incentives, promotions on products, additional products, and the like to the user based on the sensor data and the customized user output.

The computing device (e.g., a personal mobile device, insurance system server, etc.) may operate in a networked environment 100 supporting connections to one or more remote computers, such as terminals 141, 151, and 161. Such terminals may be personal computers or servers 141 (e.g., home computers, laptops, web servers, database servers), mobile communication devices 151 (e.g., mobile phones, tablet computers, etc.), wearable devices (e.g., watches, fitness tracker devices, augmented reality devices, etc.) and the like, each of which may include some or all of the elements described above with respect to the customized output generation computing device 101. The network connections depicted in FIG. 1 include a local area network (LAN) 125 and a wide area network (WAN) 129, and a wireless telecommunications network 133, but may also include other networks. When used in a LAN networking environment, the customized output generation computing device 101 may be connected to the LAN 125 through a network interface or adapter 123. When used in a WAN networking environment, the customized output generation computing device 101 may include a modem 127 or other means for establishing communications over the WAN 129, such as network 131 (e.g., the Internet). When used in a wireless telecommunications network 133, the customized output generation computing device 101 may include one or more transceivers, digital signal processors, and additional circuitry and software for communicating with wireless computing devices 151 and 161 (e.g., mobile phones, portable user computing devices, etc.) via one or more network devices 135 (e.g., base transceiver stations) in the wireless network 133.

Also illustrated in FIG. 1 is a security and integration layer 160, through which communications are sent and managed between the customized output generation computing device 101 (e.g., a personal mobile device, an intermediary server and/or external data source servers, etc.) and the remote devices (141, 151, and 161) and remote networks (125, 129, and 133). The security and integration layer 160 may comprise one or more separate computing devices, such as web servers, authentication servers, and/or various networking components (e.g., firewalls, routers, gateways, load balancers, etc.), having some or all of the elements described above with respect to the customized output generation computing device 101. As an example, a security and integration layer 160 of the customized output generation computing device 101 may comprise a set of web application servers configured to use secure protocols and to insulate the customized output generation computing device 101 from external devices 141, 151, and 161. In some cases, the security and integration layer 160 may correspond to a set of dedicated hardware and/or software operating at the same physical location and under the control of same entities as the customized output generation computing device 101. For example, layer 160 may correspond to one or more dedicated web servers and network hardware. In other examples, the security and integration layer 160 may correspond to separate hardware and software components which may be operated at a separate physical location and/or by a separate entity.

As discussed below, the data transferred to and from various devices in a system 100 may include secure and sensitive data, such as insurance policy data, and confidential user data. Therefore, it may be desirable to protect transmissions of such data by using secure network protocols and encryption, and also to protect the integrity of the data when stored on the various devices within a system, such as personal mobile devices, insurance servers, external data source servers, or other computing devices in the system 100, by using the security and integration layer 160 to authenticate users and restrict access to unknown or unauthorized users. In various implementations, security and integration layer 160 may provide, for example, a file-based integration scheme or a service-based integration scheme for transmitting data between the various devices in an electronic display system 100. Data may be transmitted through the security and integration layer 160, using various network communication protocols. Secure data transmission protocols and/or encryption may be used in file transfers to protect the integrity of the data, for example, File Transfer Protocol (FTP), Secure File Transfer Protocol (SFTP), and/or Pretty Good Privacy (PGP) encryption. In other examples, one or more web services may be implemented within the various devices in the system 100 and/or the security and integration layer 160. The web services may be accessed by authorized external devices and users to support input, extraction, and manipulation of the data between the various devices in the system 100. Web services built to support a personalized display system may be cross-domain and/or cross-platform, and may be built for enterprise use. Such web services may be developed in accordance with various web service standards, such as the Web Service Interoperability (WS-I) guidelines. In some examples, data may be implemented in the security and integration layer 160 using the Secure Sockets Layer (SSL) or Transport Layer Security (TLS) protocol to provide secure connections between the customized output generation computing device 101 and various clients 141, 151, and 161. SSL or TLS may use HTTP or HTTPS to provide authentication and confidentiality. In other examples, such web services may be implemented using the WS-Security standard, which provides for secure SOAP messages using Extensible Markup Language (XML) encryption. In still other examples, the security and integration layer 160 may include specialized hardware for providing secure web services. For example, secure network appliances in the security and integration layer 160 may include built-in features such as hardware-accelerated SSL and HTTPS, WS-Security, and firewalls. Such specialized hardware may be installed and configured in the security and integration layer 160 in front of the web servers, so that any external devices may communicate directly with the specialized hardware.

Although not shown in FIG. 1, various elements within memory 115 or other components in system 100, may include one or more caches, for example, CPU caches used by the processing unit 103, page caches used by the operating system 117, disk caches of a hard drive, and/or database caches used to cache content from database 121. For embodiments including a CPU cache, the CPU cache may be used by one or more processors in the processing unit 103 to reduce memory latency and access time. In such examples, a processor 103 may retrieve data, such as sensor data, or other types of data from or write data to the CPU cache rather than reading/writing to memory 115, which may improve the speed of these operations. In some examples, a database cache may be created in which certain data from a database 121 is cached in a separate smaller database on an application server separate from the database server (e.g., at a personal mobile device or intermediary network device or cache device, etc.). For instance, in a multi-tiered application, a database cache on an application server can reduce data retrieval and data manipulation time by not needing to communicate over a network with a back-end database server. These types of caches and others may be included in various embodiments, and may provide potential advantages in certain implementations, such as faster response times and less dependence on network conditions when transmitting and receiving driver information, vehicle information, location information, and the like.

It will be appreciated that the network connections shown are illustrative and other means of establishing a communications link between the computers may be used. The existence of any of various network protocols such as Transmission Control Protocol (TCP)/Internet Protocol (IP), Ethernet, FTP, HTTP and the like, and of various wireless communication technologies such as Global System for Mobile Communication (GSM), Code Division Multiple Access (CDMA), WiFi, and WiMAX, is presumed, and the various computing devices described herein may be configured to communicate using any of these network protocols or technologies.

Additionally, one or more application programs 119 may be used by the various computing devices, including computer executable instructions for receiving and analyzing various signals or transmissions. In some examples, the one or more application programs 119 may be downloaded or otherwise provided to a device (e.g., from a central server or other device) and may execute on the device.

Figure 2:
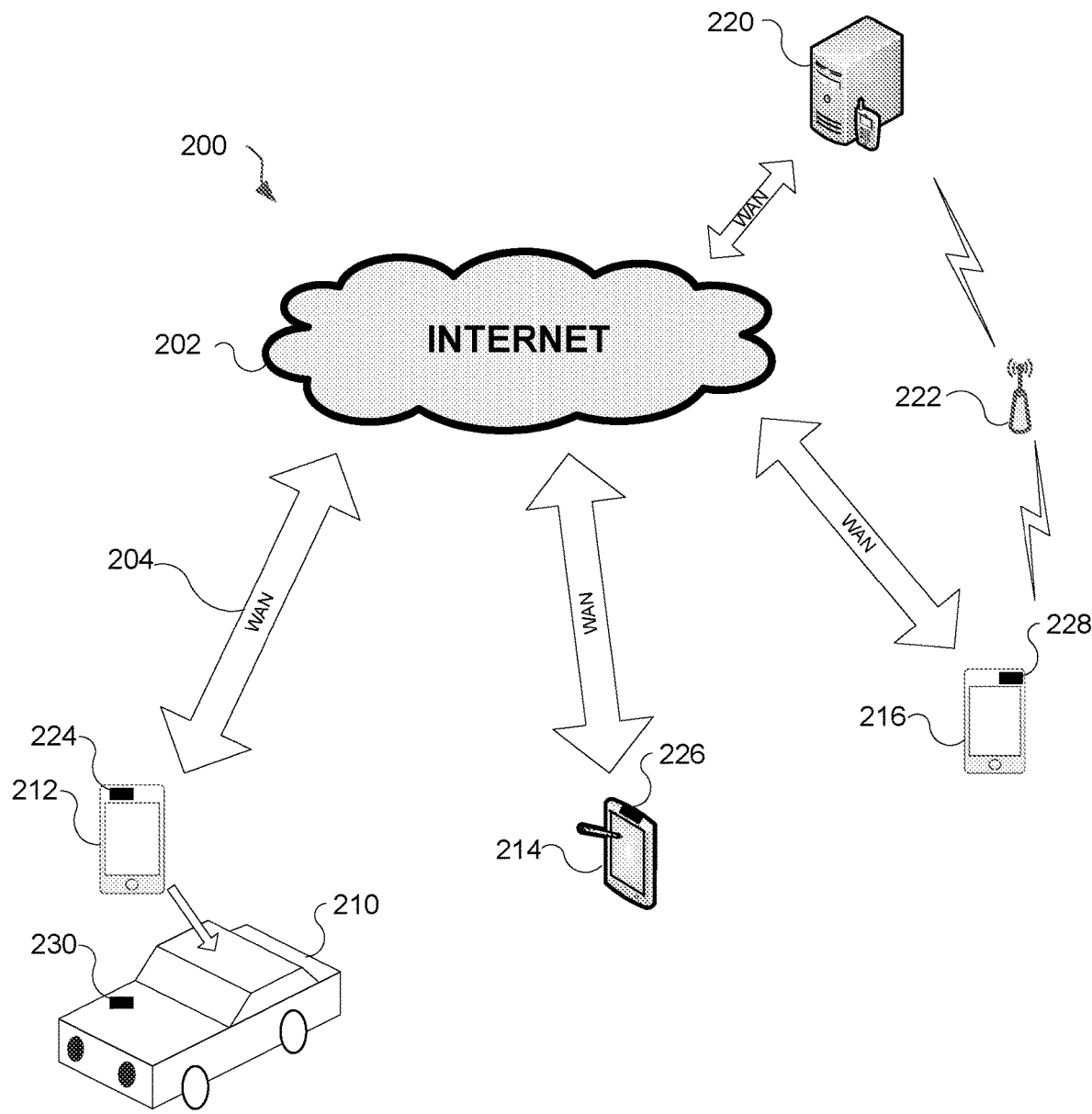
FIG. 2 shows a block diagram of a Wide Area Network (WAN) networking environment, including a network (e.g., the Internet) or other means for establishing communications over the WAN network in accordance with one or more aspects described herein.

FIG. 2 shows a block diagram of a WAN networking environment 200, including a network 202 (e.g., the Internet) or other means for establishing communications over the WAN network 204 in accordance with one or more aspects described herein. The network 202 may be any type of network and may use one or more communication protocols (e.g., protocols for the Internet (IP), Bluetooth, cellular communications, satellite communications, and the like) to connect computing devices and servers within the networking environment 200 so they may send and receive communications between each other. In particular, the network 202 may include a cellular network and its components, such as cell towers. Accordingly, for example, a mobile device 212 (e.g., a smartphone) of a driver associated with vehicle 210 may communicate, via a cellular backhaul of the network 202, with another mobile device, e.g., tablet 214, smartphone 216.

The mobile devices 212, 214, 216 may communicate back and forth over the Internet, such as through a server 220. When used in a WAN networking environment 200, the server 220 may include one or more transceivers, digital signal processors, and additional circuitry and software for communicating with wireless mobile devices (e.g., smart phone 216) via one or more network devices 222 (e.g., base transceiver stations) in the wireless network.

Mobile devices 212, 214, 216 may be, for example, mobile phones, personal digital assistants (PDAs), tablet computers, smartwatches, and other devices that may be carried by drivers inside or outside of the vehicle 210. The mobile devices 212, 214, and 216 may comprise the sensors 224, 226, 228 respectively. The sensors 224, 226, 228 may comprise motion sensors (accelerometers, speedometers, compasses, gyroscopes, and/or global positioning system (GPS) receivers, and the like, acoustic sensors (microphones and the like), vibration sensors (seismometers and the like), environmental sensors, temperature sensors (thermometers and the like), light sensors, and the like. The sensors 224, 226, 228 may comprise certain sensors that may collect and analyze sensor data over time, for example, cameras, proximity sensors, and various wireless network interfaces capable of detect access to different data networks, mobile networks, and other mobile devices (e.g., via Bluetooth). The mobile devices 212, 214, 216 may use the sensors 224, 226, 228 respectively to collect sensor data such as position, distance, speed, acceleration, orientation, speech, weather patterns, moisture, humidity, temperature, amount of light, and the like. The sensors 224, 226, 228 may comprise the same or different types of sensors. Furthermore, GPS receivers may optionally be integrated into any of the mobile devices 212, 214, 216.

The mobile devices 212, 214, 216 may be a user device as described above (e.g., a smartphone, personal digital assistant, or tablet computer, etc.), and also may include a vehicle interface component to allow the mobile device to establish communication with an on-board vehicle system. For example, either the mobile device 212, 214, 216 or a vehicle 210 may be implemented with hardware (e.g., an input port or docking station) and/or software (e.g., network interfaces, secure protocols and encryption, etc.), and may be designed and configured to establish communication (using a wired or wireless connection) between the mobile devices 212, 214, 216 and an on-board vehicle system. For example, a smartphone or tablet computer, which is often carried by a user, may include an on-board vehicle system interface to detect and/or connect to an on-board vehicle system whenever the user is driving (and/or riding as a passenger) in a vehicle. After a mobile device 212, 214, 216 establishes communication with an on-board vehicle system, which may be a telematics device, on-board diagnostic system, vehicle navigation device, or other vehicle computer system, the mobile device 212, 214, 216 may receive vehicle sensor data (e.g., acceleration data) collected by various vehicle sensors. Thus, non-vehicle based mobile devices (e.g., smartphones or tablet computers) may use vehicle interfaces to receive some or all of the same vehicle sensor data and driving data that is accessible to on-board vehicle systems, discussed below.

Vehicle 210 may be, for example, an automobile, truck, motorcycle, scooter, bus, recreational vehicle, boat, or other vehicle for which sensor data may be collected and analyzed by the mobile device. The vehicle 210 may comprise one or more vehicle sensors such as the sensor 230. For example, the sensor 230 may correspond to a telematics device, vehicle computer, and/or on-board diagnostics systems. The vehicle sensors may comprise, movement sensors including hardware and/or software components configured to detect vehicle driving data. For example, the vehicle sensors may detect and store sensor data corresponding to the vehicle's speed, distances driven, rates of acceleration or braking, and specific instances of sudden acceleration, braking, and swerving. The vehicle sensors also may detect and store sensor data received from the vehicle's internal systems, such as headlight usage, brake light operation, door opening and closing, door locking and unlocking, cruise control usage, hazard lights usage, windshield wiper usage, horn usage, turn signal usage, seat belt usage, phone and radio usage within the vehicle, maintenance performed on the vehicle, and other sensor data collected by the vehicle's computer systems. Additional vehicle sensors may detect and store sensor data relating to the maintenance of the vehicle, such as the engine status, oil level, engine coolant temperature, odometer reading, the level of fuel in the fuel tank, the level of charge in the battery (e.g., for hybrid or electric cars), engine revolutions per minute (RPMs), and/or tire pressure. Certain vehicles also may include cameras and/or proximity sensors capable of recording conditions inside or outside of the vehicle, as well as sensors configured to collect sensor data associated with a driver's movements or the condition of a driver, for example, sensors that monitor a driver's movements, such as the driver's eye position and/or head position, etc. Additional safety or guidance-assistance features may be included in some vehicles, detecting and storing sensor data such as lane departures, adaptive cruise control activation, blind spot detector activation, etc.

Figure 3:
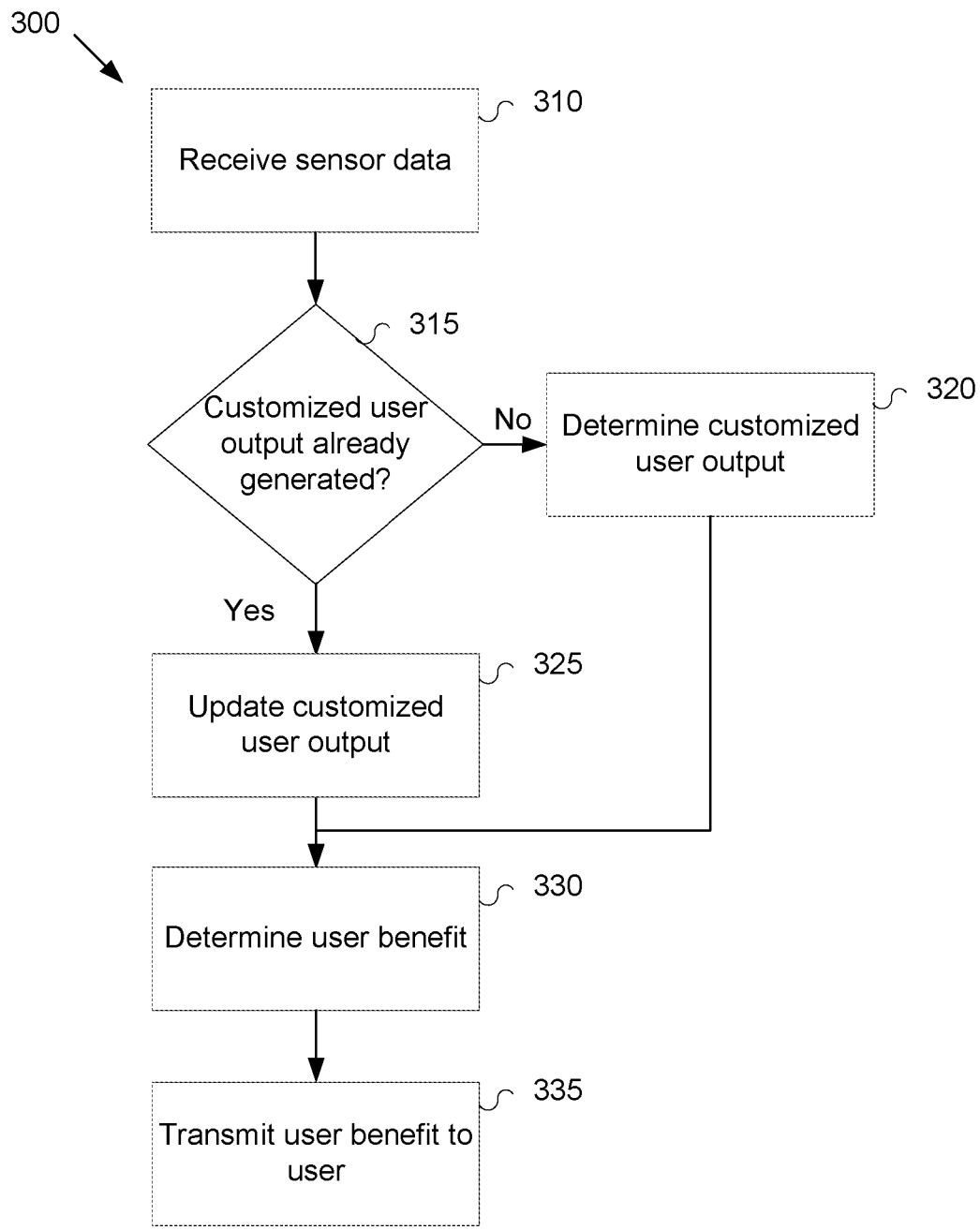
FIG. 3 is a flow diagram illustrating an example method for determining a customized user output in accordance with one or more aspects described herein.

FIG. 3 is a flow diagram illustrating an example method for determining a customized user output in accordance with one or more aspects described herein. The method 300 or one or more steps thereof may be performed by one or more computing devices or entities. For example, portions of the method 300 may be performed by components of the system 100 or the WAN networking environment 200. The method 300 or one or more steps thereof may be embodied in computer-executable instructions that are stored in a computer-readable medium, such as a non-transitory computer readable medium. The steps in this flow diagram need not all be performed in the order specified and some steps may be omitted or changed in order. The customized user output may be determined based on information received from a plurality of computing devices associated with a user, and may be used to determine a user benefit such as an incentive and/or a recommendation for additional products.

At step 310, a server, such as the server 220, may receive data related to the user. The data may be related to health, transportation, social life, a home, security, finance, and the like. The data may comprise sensor data. In one example, the server 220 may collect the health sensor data from a fitness tracker such as a wearable device configured to collect fitness or other wellness information. The server 220 may also retrieve, from a health database, the health data of the user. The data might not comprise sensor data. For example, the data may be input by a user. Further, the server 220 may receive a user input, comprising the health data, via an interactive user interface comprising a user device. In these examples, the server 220 may determine how many calories the user has burned over the course of the day, an average heart rate, whether the user is an active person or is typically stagnant, a quality of the user's sleep, and the like. The server 220 may also receive data corresponding to the user's predisposition to disease, medicines that the user takes, the user's current health issues, and the user's blood type. The server 220 may determine or estimate, based on the health sensor data, a level of stress that the user is currently experiencing. For example, the server 220 may determine that a user is stressed based on data such as: fitness data indicating on a sudden lapse in exercise, heart rate sensor data indicating a higher than normal heart rate, and/or sleep sensor data indicating restless sleep. As discuss further herein, the server 220 may also use machine learning datasets to determine overall health of the user.

The server 220 may retrieve transportation data of the user from credit card records, global positioning system data, vehicle sensor data, and/or a mobile device sensor data from mobile devices such as mobile devices 212, 214, 216. The server 220 may also retrieve, from a transportation database, transportation data of the user. Further, the server 220 may receive a user input, comprising transportation data, via an interactive user interface comprising a user device. For example, the server 220 may determine based on the transportation data whether the user typically commutes via a car, a scooter, a train/subway, a bus, a bike, and/or a rideshare application.

The server 220 may also retrieve social data from a mobile device of the user, such as mobile devices 212, 214, 216, and/or from an event calendar. This social data may be determined by a computing device (e.g., overheard by a voice recognition associated with a virtual personal assistant). The server 220 may also retrieve, from a social database and/or a social media website, social data. Further, the server 220 may receive a user input, comprising the social data, via an interactive user interface comprising a user device. For example, the social data may comprise information such as whether the user spends most of his/her time alone at home sitting on the computer, or spends most of the time going to different activities. In another example, the social data may comprise information such as whether the user frequents bars, and if so, whether he/she prefers spending time at bars as opposed to spending time at the library. In yet another example, the social data may comprise information pertaining to a relationship status, such as whether the user is single, in a relationship, married, a parent, etc.

The server 220 may collect data associated with one or more homes or other residences of the user based on, for example, Global Positioning System (GPS) tracking information, input from smart appliances, and/or other computing devices such as voice recognition devices, virtual personal assistants, and the like. The server 220 may also retrieve, from a residential database, residential data. Further, the server 220 may receive a user input, comprising the residential data, via an interactive user interface comprising a user device. For example, the server 220 may collect information such as where the user lives (crime statistics fall short of a predetermined threshold, crime statistics exceed a predetermined threshold, etc.), what type of residence he/she lives in (townhouse, condo, apartment, single family home, etc.), how much time the user spends at home versus how much time he/she is away, what appliances the user uses, which rooms the user spends the most time in, how secure the home is (whether the security system is used, door frequently kept unlocked, etc.).

The server 220 may collect security sensor data of the user based on, for example, travel records, GPS tracking information, and information from other computing devices. The server 220 may also retrieve, from a security database, security data. Further, the server 220 may receive a user input, comprising security data, via an interactive user interface comprising a user device. For example, the server 220 may collect information such as how secure a user's home is, whether he/she comes home late at night or early in the day, whether the user lives in a dangerous area, where the user travels, how much money the user typically carries around, whether doors and windows are locked, and how security averse the user is (e.g., how careful is user with disclosing personal information online). The server 220 may receive this information from, for example, smart homes and/or smart home appliances which may monitor and collect data including electricity usage, gas usage, door locks (how often are different doors locked vs. unlocked, and the like), window locks (how often are different windows locked vs. unlocked, are windows frequently left open during inclement weather, and the like), use of lighting (how often lights are turned on vs. turned off, and the like), water damage, structural damage, age of appliances, wear on structural elements/appliances, and the like.

The server 220 may collect financial sensor data of the user based on, for example, online bank records. The server 220 may also retrieve, from a financial database, financial data. Further, the server 220 may receive a user input, comprising financial data, via an interactive user interface comprising a user device. For example, the server 220 may determine current savings, loans, mortgages, investments, and net monetary value associated with the user. In another example, the server 220 may determine what financial products a user has (e.g., most money is sitting in bank savings account versus heavily invested in risky stocks).

The data received at step 310 may be stored on a server such as the server 220. For example, the data received at step 310 may be aggregated and stored in a database on the server 220.

The sensor data received at step 310 may be received from a plurality of users, sources, etc. and may be analyzed to generate one or more machine learning datasets. For example, a user may be able to provide the sensor data via a web based application, in response to a questionnaire, and the like. In these embodiments, data may not be input, collected or tracked by the sensor, but by the user himself/herself. The server 220 may link activities of a user to different stress levels, outputs, or other determinations. As additional sensor data is received by the server 220, the additional sensor data may be aggregated and compared to the machine learning datasets. This server 220 may use this comparison to determine the customized user output. This machine learning aspect is described further below with regards to FIG. 7.

At step 315, the server 220 may determine whether a customized user output has already been generated for the user. For example, the server 220 may determine whether it has stored a previously calculated value that is representative of a customized user output based on previously collected or analyzed data associated with the user.

If the server 220 determines that it did not previously generate the customized user output, the server 220 may proceed to step 320, and may calculate or otherwise determine the customized user output based on, for example, the data collected at step 310. For example, a connected health output may be generated based on all of the available health data associated with the user. In another example, a connected transportation output may be calculated based on the available transportation data associated with the user. In yet another example, a connected social output may be calculated based on the available social data associated with the user. In yet another example a connected residential output may be generated based on the available residential data. In yet another example, a connected security output may be generated based on the available security data. In yet another example, a connected financial output may be generated based on the available financial data. The server 220 may determine, via machine learning algorithms, a weight for each output. For example, the server 220 may determine the weighting based on measures of user satisfaction (e.g., users may stop using the application if certain connected outputs are too highly weighted). The server 220 may determine the weighting based on real world results (e.g., increase/decrease in health problems/car accidents). The server 220 may cluster users based on location, age, interests, and the like and may assign different weightings to different clusters. The server 220 may determine the weighting based on products sold/revenue (e.g., if many products are sold and/or revenue is high with a given weighting, the weighting may not be altered whereas if sales and/or revenue are low with a given weighting, it may be adjusted). The server 220 may determine the weighting based on a sum of accident payments (e.g., if payments are lower than an anticipated value, weighting stays the same, whereas if payments are higher than an anticipated value, weighting changes). In another example, the server 220 may allocate data as it sees fit. For example, the server 220 may allocate the same weighting to each connected output (e.g., five connected outputs, each comprises 20% of the customized user output). The server 220 may also determine this allocation via input from a user. For example, the user may input, via a user interface comprising a mobile device, a weight for different outputs. Additionally, a user may care more about one connected output in comparison to another (e.g., very financially conscious but not health conscious). In this case, the user may specify a higher weighting for the connected finance output than the connected health output. Additionally, a user may specify weighting within the calculation of the different connected outputs. For example, with respect to the connected health output, a user may want exercise sensor data to comprise 70% of the connected health output, and pre-existing health conditions to comprise 30%. In this example, sensor data such as steps per day, calories burned, and time spent in the gym may be weighed heavier than factors such as current prescriptions or medical history when determining the connected health output.

These outputs may be aggregated to create the customized user output. For example, the server 220 may combine the connected health output, the connected transportation output, the connected social output, the connected residential output, the connected security output, and the connected financial output to compute the customized user output. In one example, the server 220 may compute the customized user output based on a pre-existing algorithm. In another example, the server 220 may compute the customized user output based on allocations input by the user. In this example, the user may wish to have his or her connected health output hold be weighted more heavily than the other outputs. In this example the user may input, via an application on a mobile device such as mobile device 216, a percentage of the customized user output to be comprised by the connected health output (e.g., 30%).

If the server 220 determines that a customized user output was previously generated, the server 220 may proceed to step 325, and may update the personalized output via a method similar to that described above with regards to step 320. For example, the connected health output may be updated based on new available health data associated with the user. In another example, the connected transportation output may be calculated based on new available transportation data associated with the user. In yet another example, the connected social output may be calculated based on new available social data associated with the user. In yet another example the connected residential output may be generated based on new available residential data. In yet another example, the connected security output may be generated based on new available security data. In yet another example, the connected financial output may be updated based on new available financial data. In some examples, the system (e.g., server 220) may adjust the allocation for each output. Additionally or alternatively, a user may adjust the allocation for each output via a user input. A time and date corresponding to the previously generated customized user output may be determined. For example, a timestamp indicating when the previously generated customized user output was last updated may be stored with the customized user output. The customized user output may then be updated using sensor data that has become available since the last update to the customized user output. After the customized user output has been updated, a new timestamp may be stored that indicates when the customized user output was updated. The user may have an option to monitor the customized user output within a pre-determined time interval. In some embodiments, irrespective of whether the customized user output has changed, the customized user output may still be indicated to the user after that pre-determined time interval has lapsed.

At step 330, the server 220 may determine a user benefit based on the customized user output. In one example, the user benefit may comprise an additional insurance product. For example, the user's customized user output may reflect that they are very social, and frequently host events. In this example, the server 220 may determine that a product comprising event insurance should be offered to the user. In another example, the user's customized user output may reflect that they frequently commute by car. In this example, the server 220 may determine that a product comprising roadside assistance should be offered to the user. In yet another example, the user's customized user output may reflect that he/she is very risk averse, and the server 220 may offer the user retirement planning and/or investment insurance. In yet another example, the personalized connected health output more reflect that the user is in poor health. In this example, the server 220 may determine supplemental health insurance to offer the user. In some examples, the determination of the user benefit may depend on the customized user output as a whole. For example, the server 220 may take into account outputs across a variety of aspects associated with the user to determine the additional insurance product. In this example, the server may take into account the user's health, transportation, social, security, financial, and residential attributes.

The user benefit may comprise an insurance incentive. For example, the customized user output may reflect that the user recently purchased a home in an area that has crime rates above a predetermined threshold. However, the customized user output may also reflect that the user is very risk averse, takes the most safe walking route home at night, and does not listen to music while walking home alone. In this example, the server 220 may determine a reduction or a rebate on his/her home insurance, based on the fact that the user takes a safe walking route and does not listen to music while walking. In another example, the customized user output may reflect that the user frequently travels and rents temporary lodging associated with poor user ratings. In this example, the server 220 may determine to increase the cost of travel insurance for the user's next trip. Based on the user's actions, the customized user output may change. For example, as a result of risk adverse behavior, the customized user output may increase, whereas as a result of high risk behavior, the customized user output may decrease.

The user benefit may comprise a user product. For example, the server 220 may determine, based on the customized user output, products that may compliment the user's habits/characteristics. For example, if the customized user output comprises sensor data suggesting that the user is an avid runner, the server 220 may offer the user a promotion on new running shoes. In another example, the server 220 may determine, based on sensor data comprising the customized user output, that the user is single, but is fairly social. Based on this determination, the server 220 may offer suggestions on dating applications or online dating services. Other examples of user products may comprise at least one of, but not limited to, a restaurant advertisement, an application for a mobile device, a subscription service (e.g., an eBook service such as Audible.com), a home product (e.g., furniture, décor, etc.), or another user product. In some examples the user benefit may comprise a promotion on the user product (e.g., 50% off, buy 1 get 1 free, etc.).

In another example, the server 220 may determine, based on the customized user output, products that might not compliment the user's habits/characteristics, but may encourage or entice the user to try something new. For example, the customized user output may comprise sensor data suggesting that the user might not travel often, but the customized user output may also comprise sensor data suggesting that the user is adventurous. In this example, the server 220 may offer the user a discount on airline tickets to a foreign country.

At step 335, the server 220 may transmit, to a mobile device associated with the user (e.g., mobile devices 212, 214, 216), the user benefit. For example, the server 220 may transmit a text message, a multimedia message, a notification, and/or an email to the mobile device.

After the server 220 transmits the user benefit, steps 310-335 may be repeated. For example, the server 220 may update the customized user output and transmit a user benefit, to the user, at predetermined intervals. In another example, the server 220 may update the customized user output and transmit a user benefit, to the user, when new sensor data is received.

Figure 4:
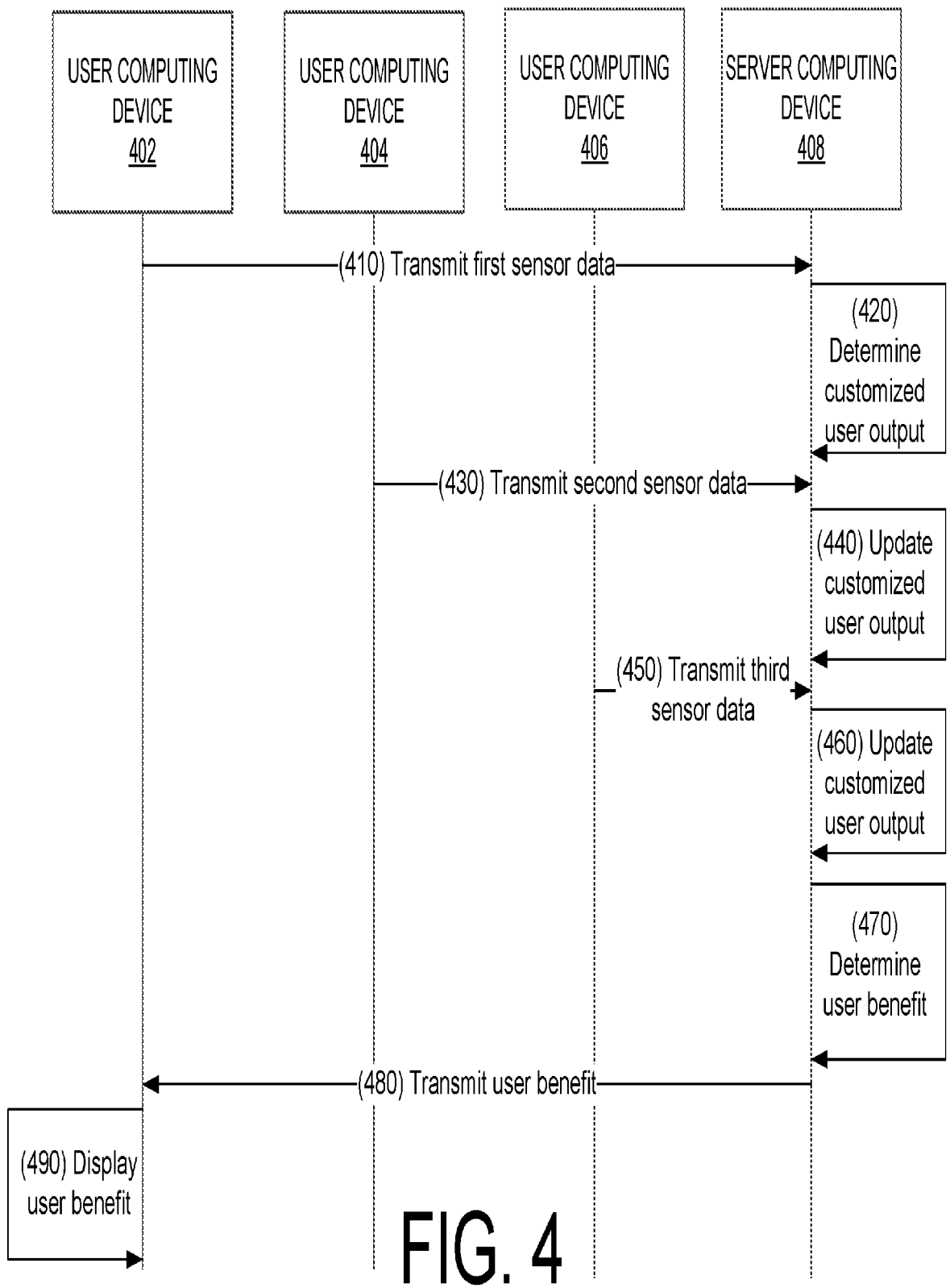
FIG. 4 depicts an illustrative event sequence for determining a customized user output and for transmitting a user benefit in accordance with one or more aspects described herein.

FIG. 4 depicts an illustrative event sequence for determining a customized user output and for transmitting a user benefit in accordance with one or more aspects described herein. While the steps shown in FIG. 4 are presented sequentially, the steps need not follow the sequence presented and may occur in any order.

At step 410, the user computing device 402 may transmit first sensor data to a server computing device 408. For example, the user computing device 402 may comprise a cell phone, a fitness tracker, a laptop computer, a GPS tracking device, a computing device, a wearable device associated with the user's vehicle, a home system, a computing device associated with a vendor (e.g., payment system unique to a particular entity, corporation, or the like), or another computing device. In this example, the server computing device may comprise the server 220. In this example, the first sensor data may comprise personal information associated with the user such as health, transportation, social, security, financial, and/or residential sensor or other data associated with the user. In one example, the first sensor data may comprise sensor data related to more than one category of personal information.

At step 420, the server computing device 408 may determine the customized user output based on the first sensor data. For example, if the first sensor data comprises health sensor data, the customized user output may reflect how healthy the user is. The customized user output may comprise for example, a number out of one hundred (e.g., 90/100 with 100 being the healthiest and 0 being the least healthy). The server computing device 408 may also determine the customized user output via machine learning algorithms as described below with regards to the method 700.

At step 430, the user computing device 404 may transmit second sensor data to the server computing device 408. For example, the user computing device 404 may comprise a cell phone, a fitness tracker, a laptop computer, a GPS tracking device, a computing device associated with the user's vehicle, a home system, a computing device associated with a vendor (e.g., payment system unique to a particular entity, corporation, or the like), or another computing device. In this example, the second sensor data may comprise personal information associated with the user such as health, transportation, social, security, financial, and/or residential sensor or other data associated with the user. In one example, the second sensor data may comprise sensor data related to more than one category of personal information.

At step 440, the server computing device 408 may update the customized user output based on the second sensor data. For example, if the first sensor data comprises health sensor data, and the second sensor data comprises transportation sensor data, the customized user output may comprise an aggregate of the health sensor data and the transportation sensor data. For example, the server computing device 408 may determine that the user walks over 10,000 steps a day on average and commutes to work on the metro. The server may update the customized user output based on both of these factors. The server computing device 408 may also update the customized user output based on machine learning analysis as described below with regards to the method 700.

At step 450, the user computing device 404 may transmit third sensor data to the server computing device 408. For example, the user computing device 404 may comprise a cell phone, a fitness tracker, a laptop computer, a GPS tracking device, a computing device associated with the user's vehicle, a home system, a computing device associated with a vendor (e.g., payment system unique to an entity, corporation, or the like), or another computing device. In this example, the third sensor data may comprise personal information associated with the user such as health, transportation, social, security, financial, and/or residential sensor or other data associated with the user. In one example, the third sensor data may comprise sensor data related to more than one category of personal information.

At step 460, the server computing device 408 may update the customized user output based on the third sensor data. For example, if the first sensor data comprises health sensor data, the second sensor data comprises transportation sensor data, and the third sensor data comprises residential sensor data, the customized user output may comprise an aggregate of the health sensor data, the transportation sensor data, and the residential sensor data. For example, the server computing device 408 may determine that the user walks over 10,000 steps a day on average, commutes to work on the metro, and lives in an area having a crime rate over a predetermined threshold. In this example, the server may update the customized user output based on this sensor data. In one example, the health sensor data, the transportation sensor data, and the residential sensor data may be each weighted the same in the customized user output (e.g., each accounts for ⅓ of the output). In another example, the health sensor data, the transportation sensor data, and the residential sensor data may be weighted differently according to user preference or preset settings on the server computing device 408. The server computing device 408 may also determine the weighting and update the customized user output based on machine learning analysis as described below with regards to the method 700.

At step 470, a user benefit may be determined by the server computing device 408. For example, a user benefit may be determined based on the customized user output that comprises an aggregate of the first sensor data, the second sensor data, and the third sensor data. In this example, the user benefit may comprise an offer for additional insurance products, an offer for additional user products, and/or a reduction/increase in the user's insurance rate. Actions performed at step 470 may be similar to those described above at step 330.

At step 480, the server computing device 408 may transmit, to the user computing device 402, the user benefit. For example, the server computing device may transmit a text message, a multimedia message, an email, and/or a notification to the user computing device 402. Actions performed at step 480 may be similar to those described above at step 335.

At step 490, the user benefit may be displayed by the user computing device 402. Although shown as being displayed at user computing device 402, the user benefit may be received and displayed at any of the user computing devices 402, 404, 406.

Figure 5:
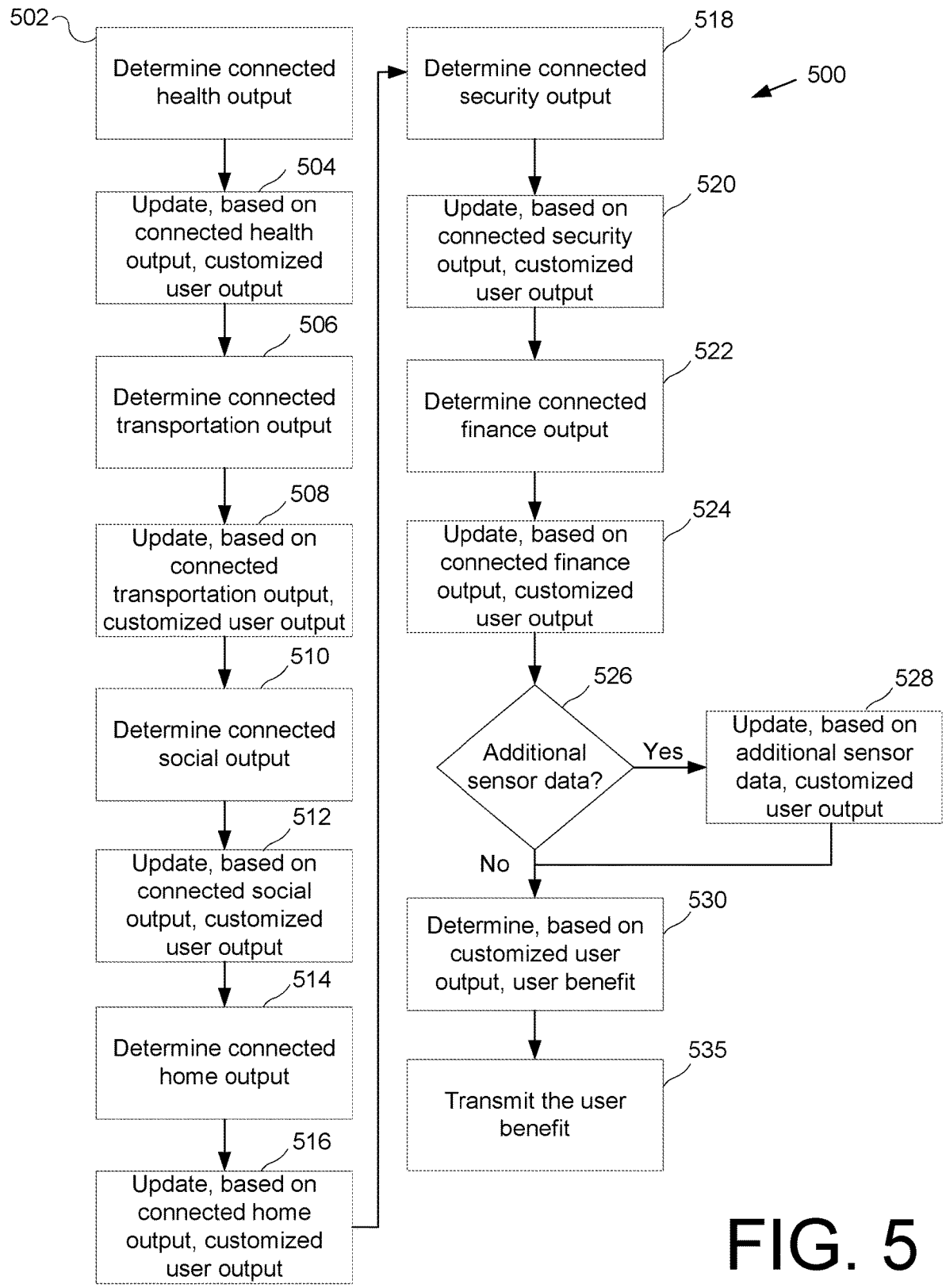
FIG. 5 is a flow diagram illustrating a method for determining a customized user output in accordance with one or more aspects describes herein.

FIG. 5 is a flow diagram illustrating a method 500 for determining a customized user output in accordance with one or more aspects described herein. The method 500 or one or more steps thereof may be performed by one or more computing devices or entities. For example, portions of the method 500 may be performed by components of the system 100 or the WAN networking environment 200. The method 500 or one or more steps thereof may be embodied in computer-executable instructions that are stored in a computer-readable medium, such as a non-transitory computer readable medium. The steps in this flow diagram need not all be performed in the order specified and some steps may be omitted or changed in order. The customized user output may be determined based on multiple pieces of sensor data associated with a user's habits/characteristics, and may be used to adjust a user benefit such as an insurance rate, a recommendation on insurance products, and/or a recommendation on additional user products. Steps 502-535 may be performed on a server, such as the server 220.

At step 502, the server 220 may determine a connected health output. The connected health output may be based on health data associated with the user. For example, the connected health output may incorporate a user's emotions (e.g., as identified via user input from the user), fitness or fitness habits, diet, hobbies, mental health, sleep, mood, medical history and/or prescriptions. The health data may be received from a plurality of computing devices such as a cell phone, a fitness tracker, a laptop computer, a GPS tracking device, a computing device associated with the user's vehicle, a home system, a vehicle voice recognition system, a computing device associated with a vendor (e.g., payment system unique to an entity, corporation, or the like), or another computing device. For example, a user may go for a run, and may use the fitness tracker to collect sensor data related to heart rate, calories burned, miles per hour, distance travelled, and the like. The fitness tracker may transmit, to the server 220, the health sensor data. If, for example, the health sensor data indicates that the user ran very slowly for a very short distance, but had a relatively high heart rate (e.g., heart rate exceeded a predetermined count/min), the server 220 may determine a low connected health output. If the health sensor data indicates that the user ran fifteen miles at a relatively fast pace (e.g., pace exceeded a predetermined speed), the server 220 may determine a high connected health output. The connected health output may be based on sensor data from more than one of the plurality of computing devices. For example, the server 220 may determine, based on health sensor data from the fitness tracker, that the user is relatively healthy (e.g., amount of workouts exceeds a predetermined count over a predetermined time period), but may determine, based on information associated with multiple vendors (e.g., an indication of where the user swiped his or her credit card) that the user is relatively unhealthy (e.g., amount of workouts falls short of the predetermined count over the predetermined time period). For example, the user's credit card history may indicate that he or she eats fast food three times per day. This may contribute to the user having a low connected health output. The health sensor data from the fitness tracker and the health sensor data from the credit card history may both be considered by the server 220 in determining the connected health output. The server 220 may also determine the connected health output based on machine learning analysis as described below with regards to the method 700.

At step 504, the server 220 may update, based on the connected health output, the customized user output. The server 220 may reduce, based on a low connected health output, the customized user output. For example, if the user is relatively unhealthy (e.g., amount of workouts falls short of a predetermined threshold over a predetermined time period), this may contribute to the user being associated with a low customized user output. The server 220 may increase, based on a high connected health output, the customized user output. For example, if the user is relatively healthy (e.g., number of workouts exceeds the predetermined threshold over the predetermined time period), this may contribute to the user being associated with a high customized user output. Sometimes, data may indicate a positive benefit in certain aspects of the customized user output, yet may indicate a negative benefit in others. For example, if a user drinks too much coffee, this may negatively impact the connected health output. However, if the user is driving in the middle of the night and is very tired, drinking coffee may help to keep the user alert and focused on the road. This may increase part of the customized user output dealing with personal safety.

The server 220 may assign a weight to the connected health output in determining the customized user output. For example, the server 220 may weigh the connected health output evenly with other variables, such as a connected transportation output, a connected social output, a connected home output, a connected security output, a connected finance output, and the like. If the server 220 considers the connected health output, along with four other variables, in determining the customized user output, each of the five variables may comprise 20% of the customized user output. The server 220 may multiply each of the five variables by 0.2, and may then add the results to determine the customized user output. This weighting may be determined using machine learning algorithms as described below with regards to the method 700.

In some examples, the user may specify a preference for weighting the connected health output in the determination of the customized user output. For example, the user may be relatively health conscious (e.g., performs at least a threshold number of workouts in a predetermined time), and health may be more important to the user than, for example, transportation. If the customized user output is determined, based on the connected health output, a connected transportation output, and three other variables, the server 220 may determine the connected health output comprises 30% of the customized user output, the connected transportation output comprises 10% of the customized user output, and each of the three other variables comprise 20% of the customized user output. The user may specify the preference via, for example, a user input on a mobile device or computer. The server 220 may also independently determine, based on an amount of health sensor data received in comparison to other sensor data received, that the user may be fairly health conscious, and the server 220 may increase the weighting of the connected health output in the determination of the customized user output. For example, the server 220 may receive a significant amount of sensor data from a fitness tracker associated with the user. Additionally, the user may have several exercise and diet applications installed on his or her mobile phone, and may frequently log workouts/calories. As a result, the server 220 may choose to increase the weighting of the connected health output in the determination of the customized user output. A user device may prompt the user to indicate if he or she would like to accept the weighting, independently determined by the server 220, or if he or she would like to decline the weighting. The user device may transmit, to the server 220 an answer to the prompt, and the server 220 may adjust or not adjust based on the answer.

Steps 502 and 504 may be repeated at any time throughout the method 500. For example, although steps 502 and 504 are shown the beginning of the method 500, the server 220 may continually monitor one or more devices to obtain updated data and/or update the customized user output based on the additional or newly collected health sensor data, received from at least one of the plurality of computing devices. The server 220 may update, at predetermined intervals, the customized user output based on new health sensor data, received from at least one of the plurality of computing devices. The server 220 may update the customized user output based on a lack of new health sensor data. For example, if the user was previously going for runs every day, as indicated to the server 220 by the user's fitness tracker, but has since stopped, the server 220 may reduce the connected health output.

At step 506, the server 220 may determine a connected transportation output. The server 220 may determine the connected transportation output based on transportation data associated with the user. For example, the connected transportation output may be based, at least in part, on data (e.g., data from one or more sensors, data retrieved from one or more databases, or the like) related to whether the user owns a car, whether the user owns more than one car, how often he/she uses the car, commuting habits associated with the user, whether the user has a ride sharing application installed on a mobile device, user ratings from the ride sharing application, how often the user uses the ride sharing application, whether the user prefers ride sharing to taking a taxi, how often the user takes taxis, a length of the user's daily commute, whether the user typically commutes by metro or train, whether the user walks to work, whether the user rides a bike to work, whether the user takes a bus to work, whether the user rides a scooter to work, a driving record associated with the user, a weekly amount of gas consumed by the user, and other similar factors.

The server 220 may receive the transportation data from a plurality of computing devices such as a cell phone (e.g., information from a ridesharing application), a laptop computer, a GPS tracking device, a computing device associated with the user's vehicle, a computing device associated with a vendor (e.g., dealership records showing purchase of a new car, gas station records showing money spent on gas, and the like), and/or another computing device. The connected transportation output may be based on a commuting time and/or a commuting cost. For example, the connected transportation output may increase with travel via bike, scooter, foot, metro, bus, and the like because such modes of transportation may allow the user to reduce travel cost. In this example, traveling via ride share, cabs, and/or a car may decrease the connected transportation output because they may be more expensive modes of transportation. A user with a clean driving record may have a higher connected transportation output than a user with a long history of accidents. If the user has a long history of accidents, the connected transportation output may increase if the user finds an alternative mode of transportation to driving. In another example, the connected transportation output may increase depending on how many modes of transportation are available to the user because having more travel options may be more convenient for the user than having one or a few travel options. For example, if a user lives near a metro stop, but also owns a bike and a car, the server 220 may associate the user with a high connected transportation output based on the number of transportation options available to the user. The server 220 may also determine the connected transportation output based on machine learning analysis as described below with regards to the method 700.

The connected transportation output may also be affected by other aspects of the customized user output. For example, if the customized user output indicates that the user is fairly unhealthy, the connected transportation output may increase if the user begins to frequently bike/walk to work. On the other hand, if the user drives or uses a ride share, the connected transportation output may decrease.

At step 508, the server 220 may update, based on the connected transportation output, the customized user output. For example, if the user has few transportation options, this may contribute to the user being associated with a low customized user output. The server 220 may increase, based on a high connected transportation output, the customized user output. For example, if the user indicates that commuting time is important to him/her, the customized user output may increase if the server 220 determines that the user started avoiding rush hour traffic by taking the metro to work. The connected transportation output may be weighed, in the calculation of the customized user output, as described above at step 504.

Steps 506 and 508 may be repeated at any time throughout the method 500. For example, the server 220 may continually update the customized user output based on new transportation sensor data, received from at least one of the plurality of computing devices. The server 220 may update, at predetermined intervals, the customized user output based on new transportation sensor data, received from at least one of the plurality of computing devices.

At step 510, the server 220 may determine a connected social output. The server 220 may determine the connected social output based on social data (e.g., sensor data, data retrieved from one or more databases, data from one or more social media sites, and the like) associated with the user. The connected social output may be an absolute value, or may be a value relative to a particular group such as a group defined by a geographic region or certain interests. For example, the connected social output may be based, at least in part, on data related to an amount of time the user spends at home versus an amount time he or she spends away from home, social media presence, whether the user has a job, whether the user is a part-time or full-time parent, whether the user is a student, social organizations the user is a part of, establishments the user frequents on the weekends, use of online dating, whether the user is in a relationship, whether the user is in a familiar city where he or she may know many people, or whether the user is traveling or recently moved to a new city and does not know many people, and the like.

The server 220 may receive the social data from a plurality of computing devices such as a cell phone, a laptop computer, a GPS tracking device, a computing device associated with the user's vehicle, a home system, a computing device associated with a vendor (e.g., payment systems show that the user frequents several downtown bars on the weekends), and/or another computing device. For example, a user's cell phone may transmit, to the server 220, the social data. The user may have several social data applications installed on the cell phone, and the user's calendar, also stored on the cell phone, may indicate that the user has many social events over the course of the week, such as dates, a book club meeting, and social events with co-workers after work. The server 220 may determine that, based on the social data, the user is relatively social (e.g., has at least a threshold number of social activities in a predetermined time period). If the server 220 receives, from the user's computer, social data such as an amount of time spent viewing social media websites (either from home or on a mobile device) but an absence of events on the user's calendar (which may also be stored on the computer), the server 220 may determine a low connected social output. The server 220 may also determine, based on an online career profile that the user is not a student, and is currently unemployed or seeking new or additional employment. This may contribute to a low connected social output. However, the server 220 may also determine that the user is a full time parent, which may cause the server 220 to associate the user with a high connected social output.

The server 220 may use customized user outputs to match users together for dates or social gatherings. In this example, the connected social output may be a large factor in matching users together. The data comprising connected social output may reflect social interests, habits/characteristics, hobbies, and the like that are associated with users. For example, the data comprising the connected social output may show that a user may prefer meeting up in a quiet coffee shop rather than a nightclub or bar. In another example, the connected social output may reflect whether a user prefers to go out or prefers to stay in. Such factors may indicate compatibility of users, and may help to inform a decision in matching users together for dates or social gatherings. The server 220 may also determine the connected social output based on machine learning analysis as described below with regards to the method 700.

At step 512, the server 220 may update, based on the connected social output, the customized user output. The server may reduce, based on a low connected social output, the customized user output. For example, if the user lives alone and rarely leaves the house, as indicated by, for example, home systems such as smart home sensors, this may contribute to a low customized user output. The server 220 may increase, in response to determining that the user is fairly social, the customized user output. The connected social output may be weighed, in the calculation of the customized user output, as described above at step 504.

Steps 510 and 512 may be repeated at any time throughout the method 500. For example, the server 220 may continually update the customized user output based on new social sensor data, received from at least one of the plurality of computing devices. The server 220 may update, at predetermined intervals, the customized user output based on new social sensor data, received from at least one of the plurality of computing devices. The server 220 may repeat, either in full or in part, the method 500.

At step 514, the server 220 may determine a connected home output. The server 220 may determine the connected home output based on home sensor data associated with the user. For example, the connected home output may incorporate how often (e.g., a percentage of time) the user is home versus away from home, appliances in the user's home and how often (e.g., percentage of time, amount of time, or the like) the user uses the appliances, how secure the home is (e.g., safety of neighborhood, is a security system installed, how often does sensor data indicate door and/or window locks are engaged, and the like), power consumption including an amount of time lights are on versus am amount of time the lights are off.

The server 220 may receive the home data from a plurality of computing devices such as a cell phone, a laptop computer, a voice recognition system associated with a virtual personal assistant, an automatic cleaning device, a home robot, a GPS tracking device, a home system (e.g., home security system, smart home systems, appliance and other smart home sensing devices, and the like), or another computing device. The user may be relatively environmentally conscious (e.g., leaves lights off in the house for at least a predetermined amount of time over a predetermined time period) and may try to frequently conserve electricity. This may lead to a high connected home output for that user. For example, the server 220 may determine, based on other aspects of the customized user output, such as the fact that the user is a member of several environmentalist organizations, that the user is relatively environmentally conscious (e.g., is a member of at least a predetermined number of environmentalist organizations), and may wish to conserve electricity. The server 220 may monitor how long the user leaves home lights on, and may adjust the connected home output accordingly. The server 220 may determine if the user has a home security system. If so, the server 220 may determine a high connected home output, if not, the server 220 may determine a low connected home output. The server 220 may take more than one variable into account in determining the connected home output. For example, a high amount of electricity conservation and an absence of a home security system may cancel each other out and may result in little or no change in the connected home output. Additionally, having one factor tending to increase the connected home output (electricity conservation), and another factor tending to decrease the connected home output (no home security system), may prevent the connected home output from being poor (e.g., 20/100 with 100 being the best, etc.), but may also prevent the connected home output from being great (e.g., 90/100 with 100 being the best, etc.). Having some factors helping and other factors hurting the connected home output may cause the connected home output to fall somewhere between poor and great (e.g. between 40/100 and 60/100 with 100 being the best, etc.). The server 220 may also determine the connected home output based on machine learning analysis as described below with regards to the method 700.

At step 516, the server 220 may update, based on the connected home output, the customized user output. The server 220 may reduce, based on a low connected home output, the customized user output. For example, if the user has a poorly-managed home (e.g., home appliances/home systems ages are above a predetermined threshold age, structural damage is above a predetermined threshold, appliances/home systems are functioning at a performance level below a predetermined threshold, and the like), this may contribute to the user being associated with a low customized user output. The server 220 may increase, based on a high connected home output, the customized user output. For example, if the user has a well-managed home (e.g., home appliances/home systems ages are below a predetermined threshold age, structural damage is below a predetermined threshold, appliances/home systems are functioning at a performance level above a predetermined threshold, and the like), this may contribute to the user being associated with a high customized user output. The connected home output may be weighed, in the calculation of the customized user output, as described above at step 504.

Steps 514 and 516 may be repeated at any time throughout the method 500. For example, the server 220 may continually update the customized user output based on new home sensor data, receiving from at least one of the plurality of computing devices. The server 220 may update, at predetermined intervals, the customized user output based on new health sensor data, received from at least one of the plurality of computing devices.

At step 518, the server 220 may determine a connected security output. The server 220 may determine the connected security output based on security data associated with the user. For example, the connected security output may be based, at least in part, on data (e.g., sensor data, data retrieved from one or more databases, etc.) related to how secure a home is, when the user usually comes home at night, where the user's house is, where the user travels, where the user stays when he or she travels, how much money the user typically caries, how careful the user is regarding personal security, how much personal information the person discloses on the internet, and the like. The server 220 may receive the security data from a plurality of computing devices such as a cell phone, a laptop computer, a GPS tracking device, a computing device associated with the user's vehicle, a home security system, a computing device associated with a vendor, a language understanding computing device, or another computing device. For example, the user may live in a somewhat dangerous area, and may come home alone late at night. The server 220 may determine this information based on a location of the home determined via a GPS, and information associated with the location of the home determined via an online database of crime statistics. The server 220 may determine that the user comes home late at night based on GPS tracking data associated with the user's cell phone. Based on this information, the server 220 may determine that the user is relatively unsafe (e.g., safety risk exceeds a predetermined threshold), and the server 220 may determine a low connected security output. If the server 220 determines that the user lives in a safe area and/or typically comes and goes during the day, the server 220 may associate a high connected security output with the user. The server 220 may also determine the connected security output based on machine learning analysis as described below with regards to the method 700.

At step 520, the server 220 may update, based on the connected security output, the customized user output. The server 220 may reduce, based on a low connected security output, the customized user output. For example, if the user is relatively unsafe (e.g., safety risk exceeds the predetermined threshold), this may contribute to the user being associated with a low customized user output. The server 220 may increase, based on a high connected security output, the customized user output. For example, if the user is relatively safe (e.g., safety risk falls short of the predetermined threshold), this may contribute to the user being associated with a high customized user output. The connected security output may be weighed, in the calculation of the customized user output, as described above at step 504.

Steps 518 and 520 may be repeated at any time throughout the method 500. For example, the server 220 may continually update the customized user output based on new security sensor data, received from at least one of the plurality of computing devices. The server 220 may update, at predetermined intervals, the customized user output based on new security sensor data, received from at least one of the plurality of computing devices.

At step 522, the server 220 may determine a connected finance output. The server 220 may determine the connected finance output based on financial data associated with the user. For example, the connected finance output may be based, at least in part, on data (e.g., sensor data, data retrieved from one or more databases, etc.) related to a user's financial products, investments, bank accounts, net worth, financial security, credit card payments, loans/loan payments and the like. The server 220 may receive the financial data from a plurality of computing devices such as a cell phone, a laptop computer, computing devices associated with vendors, computing devices associated with a user's bank, and other computing devices. For example, a user may have several investment accounts (stock, bonds, mutual funds, and the like) and several bank accounts (checking and savings). The server 220 may obtain, from at least one bank associated with the investment accounts and the bank accounts, a net worth associated with the accounts. If the net worth is high, the server 220 may determine a high connected finance output. If the net worth is low, the server 220 may determine a low connected finance output. The server 220 may determine that the user has a high net worth, based on the accounts, but also that the user has not been paying his or her credit card bill. This may result in the server 220 determining a low connected finance output despite the high net worth. The server 220 may also determine the connected finance output based on machine learning analysis as described below with regards to the method 700.

At step 524, the server 220 may update, based on the connected finance output, the customized user output. The server 220 may reduce, based on a low connected finance output, the customized user output. For example, if the user does not regularly make required payments on a loan, this may contribute to the user being associated with a low customized user output. The server 220 may increase, based on a high connected finance output, the customized user output. For example, if the user regularly makes required payments on loans, the server 220 may increase the customized user output. The connected finance output may be weighed, in the calculation of the customized user output, as described above at step 504.

Steps 522 and 524 may be repeated at any time throughout the method 500. The server 220 may continually update the customized user output based on new financial sensor data, received from at least one of the plurality of computing devices. The server 220 may update, at predetermined intervals, the customized user output based on new health sensor data, received from at least one of the plurality of computing devices.

At step 526, the server 220 may determine whether it received, from a plurality of computing devices associated with the user, additional sensor data, other than that described above at steps 502-524. If so, the server 220 may proceed to step 528. If not, the step may proceed to step 530.

At step 528, the server 220 may update, based on the additional sensor data, the customized user output. This additional sensor data may comprise sensor data that does not fit into one of the previously discussed connected outputs. For example, the additional sensor data may comprise education sensor data such as where the user is in school, degrees that the user may have, certifications that the user may have, admission test outputs associated with the user, grade point averages, and the like. Generally, if the additional sensor data tends to improve the user's quality of life, the server 220 may increase the customized user output. If the additional sensor data tends to decrease the user's quality of life, the server 220 may decrease the customized user output.

Steps 526 and 528 may be repeated at any time throughout the method 500. The server 220 may continually update the customized user output based on additional sensor data received from at least one of the plurality of computing devices. The server 220 may update, at predetermined intervals, the customized user output based on additional sensor data, received from at least one of the plurality of computing devices.

At step 530, the server 220 may determine, based on the customized user output, a user benefit. The user benefit may comprise an insurance rate adjustment. For example, the server 220 may determine that the user is a relatively safe person overall (e.g., level of safety associated with the user exceeds a predetermined threshold). The server 220 may determine this by determining that the user's customized user output exceeds above a certain threshold which may entitle the user to user benefits in the form of additional products, insurance rate adjustments, and additional insurance benefits. For example, the user may have a clean medical history (as indicated by the connected health output), a clean driving record (as indicated by the connected transportation output), a home security system (as indicated by the connected security output), and may own several financial products to ensure safety of bank accounts (as indicated by the connected finance output). As a result, the server 220 may offer, to the user, a discount on home and/or car insurance.

The user benefits may comprise a promotion associated with additional insurance products. For example, the server 220 may determine, based on the sensor and other data used to generate the customized user output (e.g., from the connected transportation output, the connected social output, the connected home output, and the like), that the user frequently travels. The server 220 may propose travel related insurance products to the user. The user benefits may comprise a promotion associated with additional non-insurance products. For example, the server 220 may determine that the user is stressed, and may offer promotions on a yoga class or a meditation application. Other examples of non-insurance products may be apparel, food, different ride hailing services, home products (replacement, augmentation, products that fit current lifestyle, products that are totally new, etc.), and other user products. For example, the server 220 may offer a promotion on a replacement home appliance, such as a new oven, and may also include a promotion on delivery and/or installation of the home appliance. The user benefits may include pricing for the item advertised. The server 220 may also determine the user benefits based on a single or multiple aspects of the customized user output. For example, the server 220 may determine a first user benefit based on the connected transportation output, and a second user benefit based on the connected health output and connected security output. The server 220 may also determine, based on the customized user output, not to transmit the user benefit. For example, the user may have a low connected transportation output, but high connected health/security outputs. Thus, the server 220 may determine a user benefit related to the connected health/security outputs, but might not determine a user benefit related to the connected transportation output.

At step 535, the server 220 may transmit, to a computing device associated with the user, the user benefit. For example, the server 220 may transmit a message, comprising the user benefit, to the user's cell phone for display to the user.

Although steps 502-535 are shown in an exemplary order in FIG. 5, steps 502-535 need not all be performed in the order specified and some steps may be omitted or changed in order. The method 500 may be a recursive method that continuously repeats. For example, the customized user output may be continually updated based on information, such as the information described above at steps 502-524, received at the server 220. The server 220 may repeat, either in full or in part, the method 500.

FIG. 6 shows an example calculation of a customized user output, such as the customized user output generated using the method 500, in accordance with one or more aspects described herein. In addition to or as an alternative to the example calculation in FIG. 6, the customized user output may also be determined using machine learning algorithms, as described below with regards to FIG. 7. A server, such as the server 220, may receive data associated with a user's health. For example, the server 220 may receive data associated with normal blood pressure and low cholesterol associated with the user. The user may have a health application on a mobile device, and may regularly check his or her blood pressure and cholesterol, and update the application accordingly. The mobile device may transmit this information to the server 220. The server 220 may receive data from a fitness tracker data (e.g., sensor data) related to number of times a user exercises (e.g., that the user typically runs three times a week, and conditions during athletic activity (e.g., has a heart rate below a predetermined threshold). The server 220 may receive sensor data from a digital scale indicating that the user has a weight within a predetermined range deemed normal for his or her height, age, etc. This sensor data suggests that the user is healthy, and accordingly, each of these data points may receive a positive point value. For example, the blood pressure, cholesterol, heart rate, weight, and running schedule may be associated with five, seven, three, eight, and ten points respectively, in this particular example. The server 220 may add these points to determine the connected health output 610, which in this case may comprise 33.

The server 220 may also receive transportation data. For example, the server 220 may receive, from an insurance claim database, an indication that the user has never been in a car accident. The server 220 may also receive data from a bank server indicating a recently approved car loan and a check authorized to a car dealership. The server 220 may determine that the user purchased a new vehicle. This data suggests that the user is a safe driver and is improving the quality of his or her daily commute by purchasing the new car. As a result, the driving record and car purchase may be associated with seven and five points respectively. The server 220 may add these points to determine the connected transportation output 620, which in this case may comprise 12.

The server 220 may also receive security data. For example, the server 220 may have no record of an affiliation between the user and a home security system/service. The server 220 may also receive GPS sensor data associated from the user's cell phone. The GPS sensor data may indicate that the user spends 80% of his or her time at a particular location, from which the server 220 may determine that the particular location is the user's home. The server 220 may cross reference the location against a crime statistics database, and may determine, based on the cross reference, that the user lives in a high crime area. The lack of security system and high crime neighborhood make the user vulnerable to a security breach and/or crime. As a result, the security system and home address may be associated with negative three and negative nine points respectively. The server 220 may add these points to determine the connected security output 630, which in this case may comprise negative twelve.

The server 220 may aggregate the allotted points for the connected health output 610, the connected transportation output 620, and the connected security output 630, and may take an average of the three to calculate a score, which then may be used to determine the customized user output 640. Thus, the server 220 may add 33+12−12=33. The server 220 may then divide 33/3 to compute the average output. As a result, in this example, the server 220 may determine a customized user output 640 of 11. Although the customized user output 640 takes into account health, transportation, and security sensor data, it should be appreciated that the customized user output 640 may comprise sensor data associated with other concepts, such as financial sensor data, home sensor data, and social sensor data.

The server 220 may compare the customized user output to a predetermined threshold. For example, the predetermined threshold may comprise thirty points. If the customized user output does exceed the predetermined threshold, the server 220 may transmit a user benefit such as a rate discount, an insurance promotion, a promotion on user product, and/or an offer for new insurance products.

Figure 7:
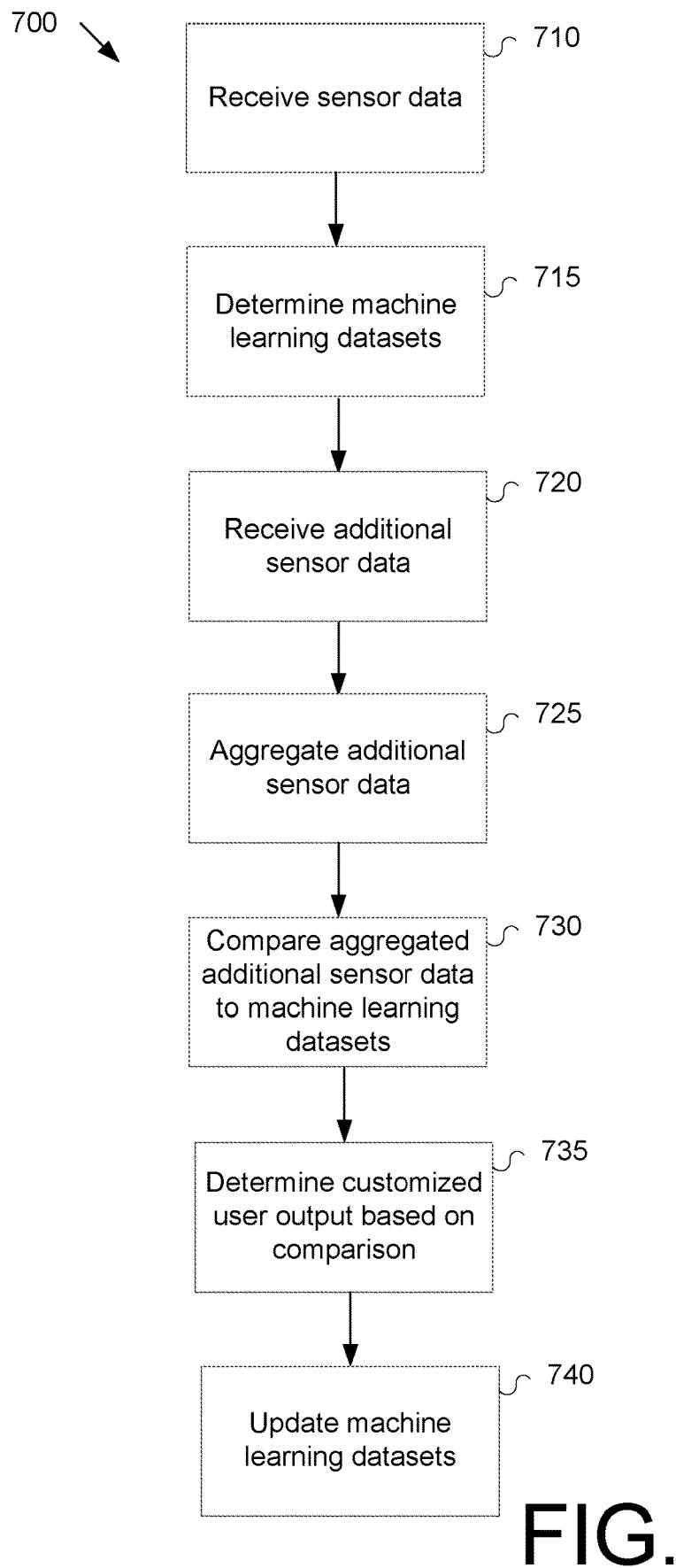
FIG. 7 shows a flow diagram for a method for determining a customized user output based on machine learning datasets in accordance with one or more aspects described herein.

FIG. 7 shows a flow diagram for a method 700 for determining a customized user output based on machine learning datasets in accordance with one or more aspects described herein. The method 700 or one or more steps thereof may be performed by one or more computing devices or entities. For example, portions of the method 700 may be performed by components of the system 100 or the WAN networking environment 200. The method 700 or one or more steps thereof may be embodied in computer-executable instructions that are stored in a computer-readable medium, such as a non-transitory computer readable medium. The steps in this flow diagram need not all be performed in the order specified and some steps may be omitted or changed in order. The method 700 may be performed by a server, such as the server 220 which may, in some examples, include a machine learning engine configured to generate one or more machine learning datasets. The server 220 may implement the method 700 in lieu of or in addition to the method 300.

At step 710, the server 220 may receive sensor data based on a plurality of characteristics from a plurality of users. The sensor data received at step 710 may comprise the sensor data described above with regards to step 310. For example, the sensor data may comprise sensor data, received from a plurality of sensors associated with a plurality of users. The sensor data may be associated with a plurality of characteristics associated with each of the plurality of users. For example, the sensor data may comprise health sensor data, transportation sensor data, social sensor data, residential sensor data, security sensor data, financial sensor data, and the like, associated with each of the plurality of users.

At step 715, the server 220 (e.g., a machine learning engine of server 220) may determine or generate, based on the sensor data, one or more machine learning datasets. The machine learning datasets may link activities of a user to different stress levels, outputs, or other determinations. For example, based on received data, one machine learning dataset may associate driving in heavy traffic with a high stress level and relaxing on a beach with a low stress level. Similarly, another machine learning dataset may link activities of a user to different levels of health, transportation, social interaction, residence, security, finance, and the like. The levels may be defined by predetermined thresholds.

At step 720, the server 220 may receive, from a sensor, additional sensor data. The additional sensor data may be associated with a particular user. The additional sensor data may be similar to the sensor data described above at step 710.

At step 725, the server 220 may aggregate the additional sensor data and any previously received sensor data associated with the particular user. This may result in aggregated sensor data. For example, the server 220 may aggregate health sensor data, transportation sensor data, social sensor data, residential sensor data, security sensor data, financial sensor data, and the like comprising the additional sensor data and the sensor data, received at step 710, associated with the particular user.

At step 730, the server 220 may compare the aggregated sensor data to the machine learning datasets. For example, the server 220 may implement machine learning algorithms to determine whether the aggregated sensor data falls short of the predetermined thresholds, exceeds the predetermined thresholds, or exceeds some of the predetermined thresholds but falls short of others. The server 220 may identify a baseline level of health, transportation, social interaction, residence, security, finance, and the like. The baseline level may comprise the predetermined threshold. The server 220 may compare a first portion of the aggregated sensor data to a first machine learning dataset and may compare a second portion of the aggregated sensor data to a second machine learning dataset. The server 220 may compare all of the aggregated sensor data to a single or multiple common datasets.

At step 735, the server 220 may determine, based on the comparison described above with regards to step 730, a customized user output. For example, the server 220 may quantify the determination of how the aggregated sensor data compares to the machine learning datasets. The customized user output may comprise the customized user output described above with regards to FIG. 3. Based on the customized user output, the server 220 may determine and transmit, to a user device, a user recommendation output. For example, this may be the user recommendation output described at steps 815, 1015, and 1215 respectively. The server 220 may also determine and transmit, to a user device, a benefit. For example, this may be the benefit described above with regards to steps 330 and 335.

At step 740, the server 220 may update or validate, based on the aggregated sensor data, the machine learning datasets.

Figure 8:
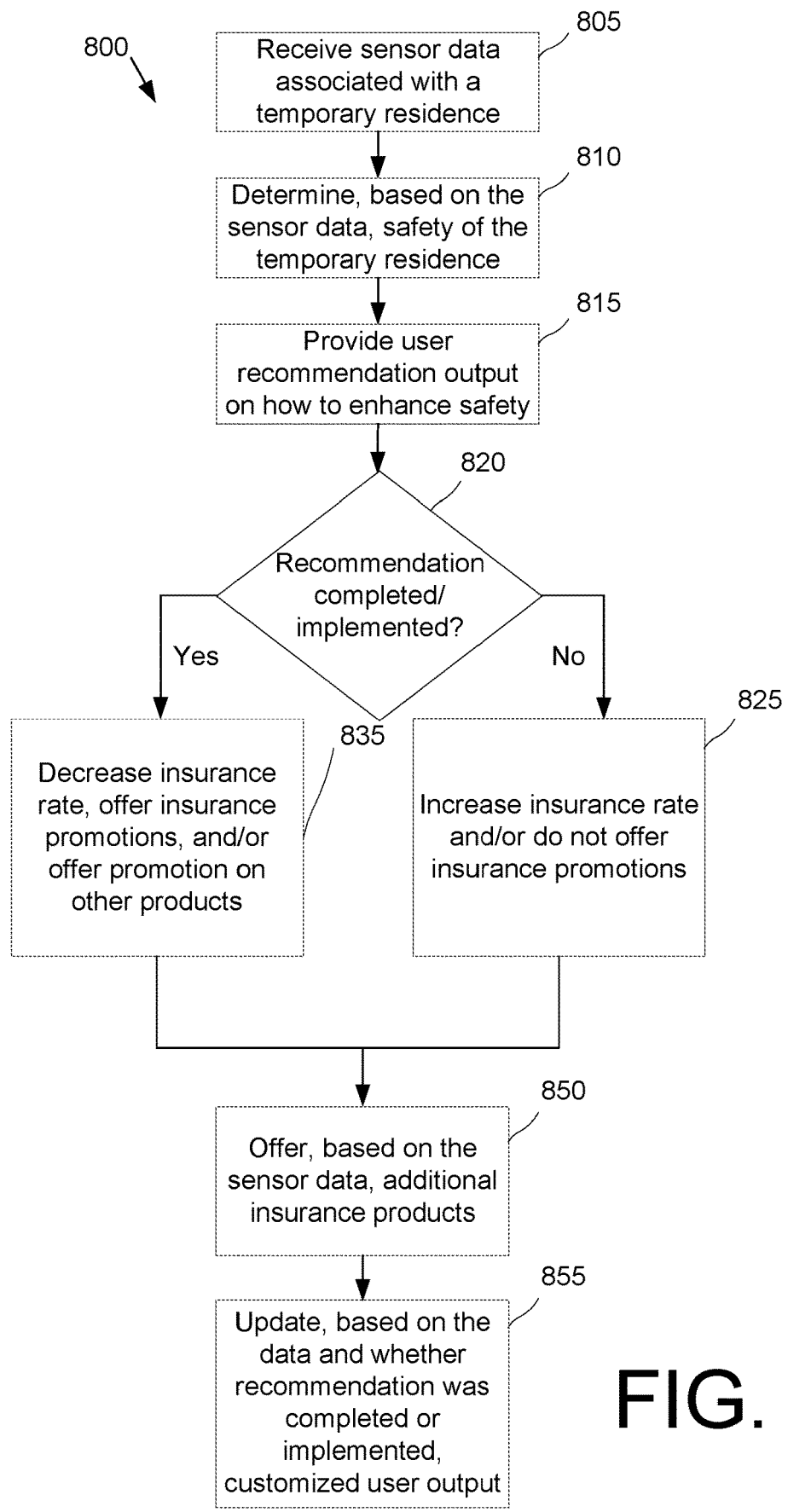
FIG. 8 shows a flow diagram for a method for determining benefits based on information associated with a temporary residence in accordance with one or more aspects described herein.

FIG. 8 illustrates a flow diagram for a method 800 for determining benefits based on information associated with a temporary residence (e.g. a travel booking) in accordance with one or more aspects described herein. The method 800 or one or more steps thereof may be performed by one or more computing devices or entities. For example, portions of the method 800 may be performed by components of the system 100 or the WAN networking environment 200. The method 800 or one or more steps thereof may be embodied in computer-executable instructions that are stored in a computer-readable medium, such as a non-transitory computer readable medium. The steps in this flow diagram need not all be performed in the order specified and some steps may be omitted or changed in order. The method 800 may be performed by a server, such as the server 220.

At step 805, the server 220 may receive data associated with a temporary residence. For example, the temporary residence may comprise at least one of: a hotel or a vacation rental property and may include short-term rental properties. The data may comprise at least one of: a location, crime statistics and information associated with the location, user ratings, cost, weather patterns and the like. The data may also comprise similar information associated with nearby temporary residences. For example, the server 220 may receive the similar information for temporary residences within a one mile radius, a two block radius, in the same building, in neighboring buildings, and the like.

At step 810, the server 220 may determine, based on the data, safety of the temporary residence. The server 220 may determine that the temporary residence comprises a vacation rental property associated with poor user ratings. The server 220 may determine that the temporary residence comprises an inexpensive (e.g., cost per day below a predetermined threshold) vacation rental property in a location associated with high crime statistics. The server 220 may determine that the temporary residence comprises a vacation rental property located in the path of destructive weather patterns or natural disasters such as a tornado, a hurricane, and the like. In these circumstances, and other similar circumstances not described, the server 220 may determine that the temporary residence may be associated with a low safety level.

At step 815, the server 220 may determine, based on a determination at step 810 that the temporary residence may be associated with a low safety level, a user recommendation output to enhance a user's safety. For example, based on a determination that the temporary residence is associated with poor user ratings, the server 220 may transmit, to a mobile device associated with the user, a message suggesting that the user lock any valuables in a safe when the user is not in the temporary residence. Based on a determination that the temporary residence is located in an area with high crime statistics, the server 220 may transmit, to a mobile device associated with the user, a message suggesting that the user not wander the nearby streets alone at night. Based on a determination that the temporary residence is in the path of destructive inclement weather, the server 220 may transmit, to a mobile device associated with the user, a message suggesting that the user leave the temporary residence early to avoid the weather. The message may suggest, alternatively or in addition, that the user move to a sheltered location (e.g., a basement, room with no windows, and the like).

At step 820, the server 220 may determine whether or not the user recommendation output was completed or implemented. For example, the user may input, to the mobile device, that he or she locked valuables in the safe prior to leaving the temporary residence. The mobile device may transmit, to the server 220, an indication that the user recommendation output to lock valuables in the safe was completed or implemented. The server 220 may also determine, based on GPS sensor data associated with the mobile device, the user stayed inside the temporary residence between 11 PM and 7 AM. Based on this information, the server 220 may determine that the user recommendation output not to wander the nearby streets alone at night was not completed or implemented. The server 220 may determine, based on an early checkout message sent to the owner of the temporary residence, that the user recommendation output to leave the temporary residence early to avoid destructive inclement weather was completed or implemented.

If the server determines that the user recommendation output was not completed or implemented, based on an indication (or lack thereof) from a user device, the server may proceed to step 825. If the server 220 determines that the recommendation output was completed, based on an indication from a user device, the user recommendation output, the server 220 may proceed to step 835.

The server 220 may determine that although the user did not completely follow the user recommendation output, at least a threshold for completion of the user recommendation output was met. For example, the user may have rented the temporary residence for a week, and may have only wandered alone outside one night. The server 220 may determine that because the user recommendation output was implemented to an extent that exceeds a predetermined threshold, the server 220 may proceed to step 835. The threshold may be set on the server 220, and may vary depending on the totality of circumstances surrounding the temporary residence.

At step 825, the server 220 may transmit, to the user, an indication of an increased insurance rate. For example, by not following the user recommendation output, the user may indicate to the server 220 that he or she is a relatively high risk (e.g., level of risk exceeds a predetermined threshold) for an insurance company, and thus the insurance company may require higher payments for coverage of the user. For example, the insurance company may increase the cost of the user's home insurance, renters insurance, travel insurance, health insurance, and/or life insurance. The server 220 may also not offer insurance promotions to the user. For example, the insurance promotions may comprise an incentive for the user to follow user recommendation output presented to the user. Thus, if the user fails to follow the user recommendation output, the user might not receive the incentive.

At step 835, the server 220 may transmit, to the user, an indication of a decreased insurance rate. For example, by following the user recommendation output, the user may indicate to the server 220 that he or she is a relatively low risk (level of risk falls short of a predetermined threshold) for the insurance company. As a result, the insurance company may reward the user by reducing the cost of the user's coverage. For example, the insurance company may increase the cost of the user's home insurance, renters insurance, travel insurance, health insurance, and/or life insurance. The server 220 may transmit, to the user, an insurance promotion. The insurance promotion may comprise a reward for implementing the user recommendation output. For example, if the user is not currently insured, the server 220 may transmit the insurance promotion to incentivize the user to purchase insurance from the insurance company. The insurance promotion may be a promotion on home insurance, medical insurance, dental insurance, car insurance, boat insurance, travel insurance, life insurance, and the like. The server 220 may transmit, to the user, a promotion on other products. For example, the promotion on other products may comprise a reward for following the user recommendation output. The other products may comprise travel related products such as a suitcase, travel lock, plane tickets, and the like. The other products may comprise non-travel related products. The additional products may correspond to aspects of the customized user output. In some examples, the additional products might not correspond to a user's current customized user output, but may be offered to enrich the user's current experience. For example, the products may prompt the user to try something new. For example, although the user may currently have a low connected health output, the server 220 may transmit an offer on new running shoes in an attempt to help the user increase his or her customized user output. The customized user output may increase or decrease depending on how often the products are used.

At step 850, the server 220 may transmit, to the user, an indication of additional insurance products. The server 220 may determine the additional insurance products based on the sensor data. The server 220 may also determine the additional insurance products based on a customized user output. For example, the customized user output may be determined via the method 500 and/or the machine learning method described above with regards to FIG. 7. The sensor data may comprise a factor in the customized user output. For example, the sensor data may indicate that the user booked a temporary residence with poor user ratings in a location with a high crime rate. The customized user output may reflect that the user frequently makes similar bookings. As a result of the customized user output and the sensor data, the server 220 may transmit an indication of an offer to purchase travelers insurance. An example of the offer is described below with regards to FIG. 8. The insurance may cover faulty aspects of the temporary residence, double-booking of the temporary residence, theft from the temporary residence, a trip in its entirety, baggage, a rental car, trip cancellation, and the like. The insurance product may also be home insurance, medical insurance, dental insurance, car insurance, boat insurance, travel insurance, life insurance, and the like. Step 850 may occur at any time during the method 800.

At step 855, the server 220 may update, based on the sensor data and based on whether the user recommendation output was completed or implemented, the customized user output. For example, if the user stayed at a temporary residence in a dangerous area and did not complete or implement the user recommendation output to keep valuables in a locked safe when out of the temporary residence, received from the server 220, the server 220 may reduce the connected security output associated with the user. This may cause a decrease in the customized user output. If the user stayed in the dangerous area, but did complete or implement the user recommendation output, the server 220 may decide neither to reduce nor to increase the connected security output associated with the user, and thus the customized user output may remain largely unaffected. Step 855 may occur at any time throughout the method 800. Furthermore, the method 800 may be repeated whenever the server receives additional sensor data regarding a temporary residence.

Figure 9:
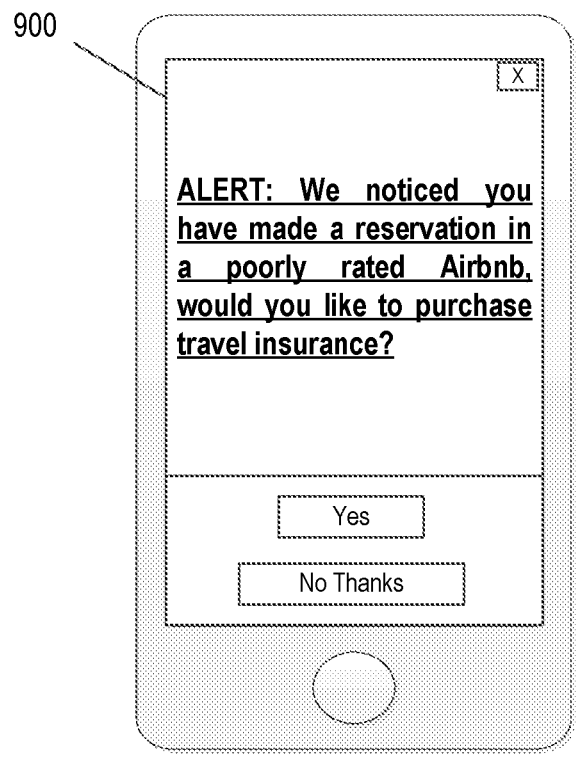
FIG. 9 shows a mobile device display in accordance with one or more aspects described herein.

FIG. 9 illustrates a mobile device display according to aspects described herein. The display 900 comprises an alert associated with a booking of a poorly rated temporary residence in accordance with one or more aspects described herein. Based on the booking, a server such as the server 220 may determine the alert and transmit, to a mobile device associated with a user, the alert. The server 220 may determine the alert based on the customized user output. For example, the server 220 may determine, based on the customized user output, a user frequently stays in poorly rated temporary residences. The server 220 may also determine the alert based on a single act, such as an online booking for a temporary residence. For example, the alert may prompt the user to purchase travel insurance. The user may select an option via user input on the display 900 such as "Yes," or "No thanks." Based on the user input, the server 220 may allow the user to purchase the travel insurance. Although FIG. 9 shows a recommendation to purchase travel insurance, the alert may comprise a recommendation to purchase a different type of insurance such as home insurance, medical insurance, dental insurance, car insurance, boat insurance, life insurance, and the like. The alert may comprise the user benefit described above with regards to steps 330, 335, 470, 480, 490, 530, and 535. Although FIG. 9 shows the display 900 of a mobile device, the alert may be displayed via a display comprising a different computing device, such as a laptop computer, personal computer, television, tablet, and the like. The alert may comprise any of a text message, an email, a notification, and the like.

Figure 10:
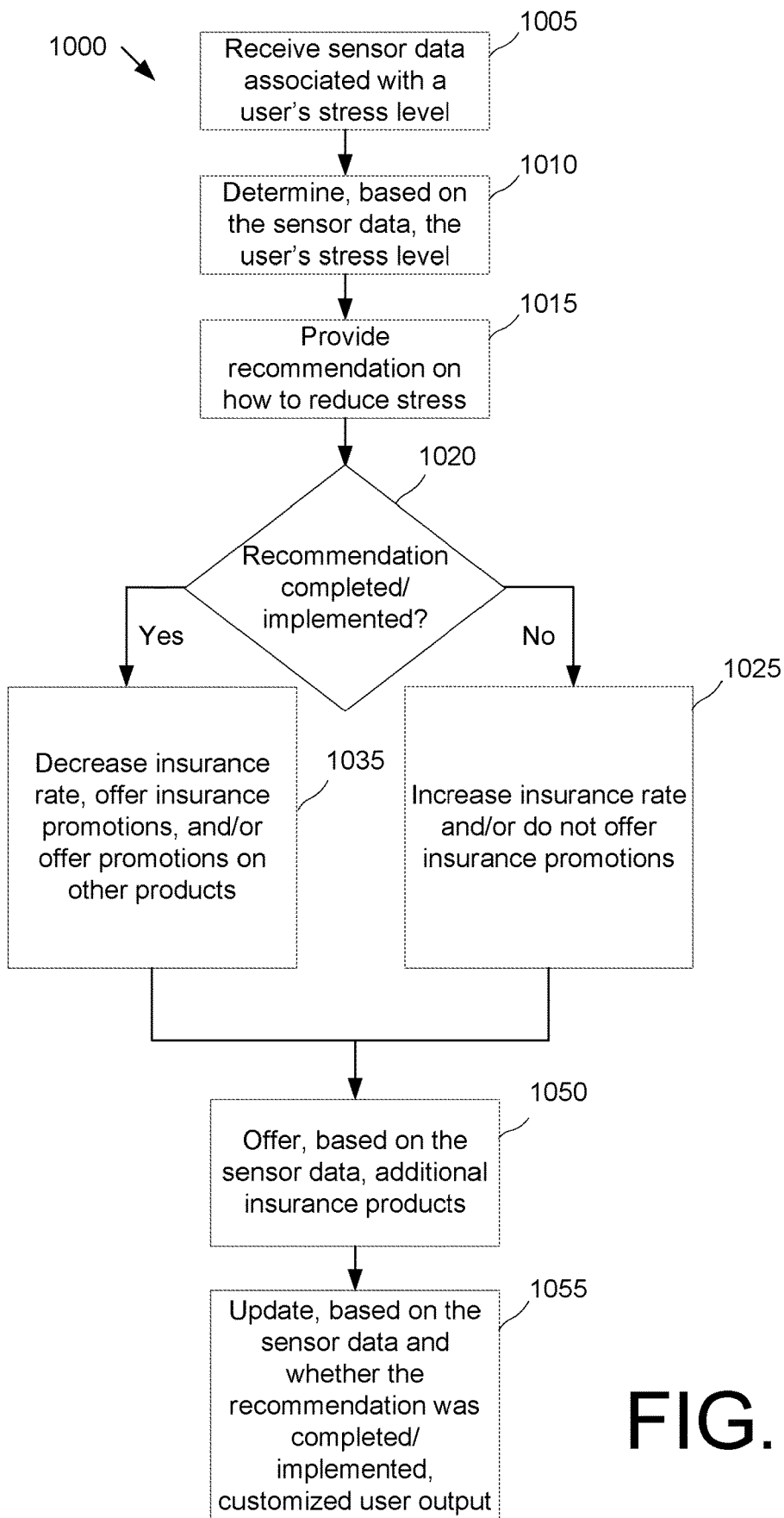
FIG. 10 shows a flow diagram for a method for determining benefits based on information associated with a temporary residence in accordance with one or more aspects described herein.

FIG. 10 shows a flow diagram for a method 1000 for determining benefits based on information associated with a temporary residence in accordance with one or more aspects described herein. The method 1000 or one or more steps thereof may be performed by one or more computing devices or entities. For example, portions of the method 1000 may be performed by components of the system 100 or the WAN networking environment 200. The method 1000 or one or more steps thereof may be embodied in computer-executable instructions that are stored in a computer-readable medium, such as a non-transitory computer readable medium. The steps in this flow diagram need not all be performed in the order specified and some steps may be omitted or changed in order. The method 1000 may be performed by a server, such as the server 220.

At step 1005, the server 220 may receive sensor data associated with a user's stress level. For example, the sensor data may comprise at least one of a user's heart rate, blood pressure, calendar information such as meetings and the like, sleep sensor data, exercise sensor data, a user input comprising a current stress level, a user's voice or tone, GPS sensor data, traffic sensor data, and the like. The server 220 may receive this sensor data from at least one of a laptop computer, a personal computer, a cell phone, a voice recognition device, a fitness tracker, and a user input to a computing device.

At step 1010, the server 220 may determine, based on the sensor data, the user's stress level. The server 220 may determine that the user's heart rate or blood pressure is unusually high, which may indicate a high level of stress. The server 220 may determine that a user's calendar is packed with important meetings on a given day, and may determine based on this schedule that the user has a high likelihood of stress. The server 220 may determine that the user has not slept much over the last several nights, or that the user was restless throughout the night. Based on this information, the server 220 may determine that the user may be stressed. GPS sensor data may indicate that the user is currently in the office, which may cause more stress than if the user is, for example, on a Caribbean vacation. The server 220 may determine a low level of stress if the sensor data comprises, for example, a clear schedule, a normal heartrate, sleep sensor data indicating quality and plentiful rest, or GPS sensor data indicating that the user is on vacation at the beach.

At step 1015, the server 220 may transmit, to the user, user recommendation output on how to reduce stress. For example, the user recommendation output may comprise a suggestion to listen to soothing music, and may comprise a message with a link to a music streaming service. The user recommendation output may comprise a suggestion to attend a yoga class, and may comprise a list of local studios. The user recommendation output may comprise a suggestion to visit a spa, and may comprise a list of local establishments. The user recommendation output may comprise a suggestion to take an alternate, possibly less congested and more scenic driving route, and may comprise a link to a navigation application. The user recommendation output may comprise a suggestion to take an extended vacation or to get out of town for the weekend, and may comprise a link to local travel agencies, or a website that offers temporary residences. The user recommendation output may also be based on a customized user output, such as the customized user output determined above via the methods 500 and 700. For example, the customized user output may include information associated with the user, and the server 220 may be able to use that information, in addition to the sensor data, to offer appropriate user recommendation output. For example, if sensor data used to create the customized user output indicates that the user is an avid yoga participant, the server 220 may be more likely to transmit a suggestion to practice yoga to reduce stress than to listen to soothing music. The user recommendation output may comprise a single suggestion, or the user recommendation output may comprise multiple suggestions. The server 220 may transmit the user recommendation output to the user via, for example, a text message, email message, notification message, and the like, and the user may view the user recommendation output on, for example, a cell phone. The user recommendation output may be displayed similar to the alert shown in FIG. 11.

At step 1020, the server 220 may determine whether the user recommendation output was completed or implemented. For example, the user may select an option, comprising the user recommendation output, to listen to soothing music, to take an alternate driving route, to take a yoga class, and the like. When the user selects the option on, for example, a mobile device, the mobile device may transmit a message back to the server 220 indicating that the user recommendation output was implemented or completed. If the user selects a different option, such as "No thanks," the mobile device may transmit a message back to the server 220 indicating that the user recommendation output was not implemented or completed. For example, the user may prefer to continue on a congested driving route. If the server 220 determines that the user recommendation output was completed or implemented, the server 220 may proceed to step 1035. If the server 220 determines that the user recommendation output was not completed or implemented, the server 220 may proceed to step 1025.

At step 1025, the server 220 may transmit, to the user, an indication of an increased insurance rate. For example, by not following the user recommendation output, the user may indicate to the server 220 that he or she is a relatively high risk (e.g., level of risk exceeds a predetermined threshold) for an insurance company, and thus the insurance company may require higher payments for coverage of the user. For example, if the server 220 determines that the user is stressed, but is continuing to drive in highly congested traffic, the user may be more likely to get into an accident than a user who is less stressed. As a result, the insurance company may increase the cost of the user's home insurance, renters insurance, auto insurance, and/or life insurance. The server 220 may also not offer insurance promotions to the user. For example, the insurance promotions may comprise an incentive for the user to follow the user recommendation output presented to the user. Thus, if the user fails to follow the user recommendation output, the user might not receive the incentive.

At step 1035, the server 220 may transmit, to the user, an indication of a decreased insurance rate. For example, by following the user recommendation output, the user may indicate to the server 220 that he or she is a relatively low risk (e.g., level of risk falls short of a predetermined threshold) for the insurance company. As a result, the insurance company may reward the user by reducing the cost of the user's coverage. For example, the insurance company may reduce the cost of, for example, the user's home insurance, renters insurance, medical insurance, life insurance, and the like. The server 220 may transmit, to the user, an insurance promotion. The insurance promotion may comprise a reward for following the user recommendation output. For example, the server 220 may transmit an insurance promotion to incentivize a new user to purchase insurance from the insurance company. The insurance promotion may be a promotion on home insurance, medical insurance, dental insurance, car insurance, boat insurance, life insurance, and the like. The server 220 may transmit, to the user, a promotion on other products. For example, the promotion on the other products may comprise a reward for following the user recommendation output. The other products may comprise music subscriptions or credits, discounts or free passes for yoga classes, gym discounts or memberships, travel incentives, deals on home electronics such a television or computer, fitness trackers, and the like. The server 220 may select the other products based on the customized user output. For example, if sensor data comprising the customized user output reflects that the user is fairly active and is interested in fitness, the server 220 may offer a promotion on a fitness tracker. The additional products may correspond to aspects of the customized user output. In some examples, the additional products might not correspond to a user's current customized user output, but may be offered to enrich the user's current experience. For example, the products may prompt the user to try something new. The customized user output may increase or decrease depending on how often the products are used.

At step 1050, the server 220 may offer, based on the sensor data, an indication of additional insurance products. The server 220 may determine the additional insurance products based on the sensor data. The server 220 may also determine the additional insurance products based on the customized user output. The sensor data may comprise a factor in determination of the personalized life. For example, the sensor data may indicate that the user has been at work for fifteen hours. The customized user output may reflect that this is typical for the user. For example, a server 220 may determine this based on GPS sensor data associated with the user's cell phone. The server 220 may offer, based on this determination, a health insurance package that covers activities such as meditation or therapy. If the user is made aware of these products, he or she may be more likely to engage in stress management treatment such as meditation or therapy.

Figure 11:
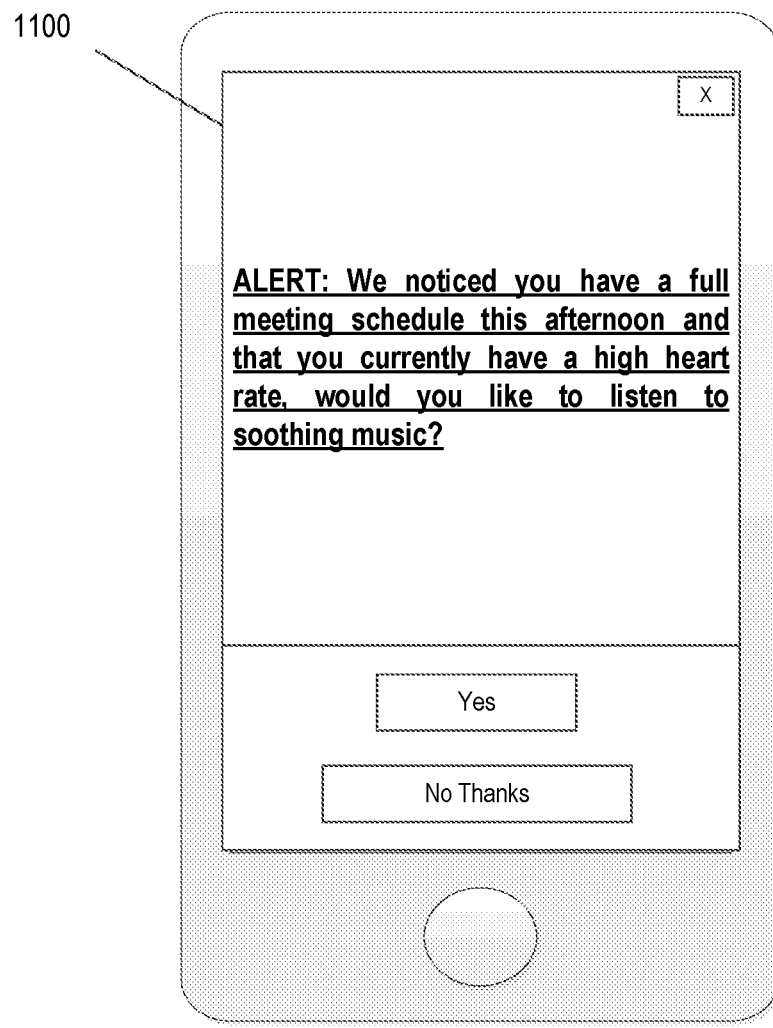
FIG. 11 shows a mobile device display in accordance with one or more aspects described herein.

The server 220 may also offer additional insurance products based on information associated with the customized user output. These additional insurance products may be unrelated to the user's stress level. For example, the server 220 may transmit, to the user's cell phone, a recommendation to purchase a different type of insurance such as home insurance, medical insurance, dental insurance, car insurance, boat insurance, life insurance, and the like, based on information associated with the customized user output. For example, if the user recently purchased an expensive home entertainment system, the server 220 may transmit an offer to insure the home entertainment system. The alert may comprise the user benefit described above with regards to steps 330, 335, 470, 480, 490, 530, and 535. Although FIG. 11 illustrates one example display 1100 of a mobile device, the alert may be displayed via a display comprising a different computing device, such as a laptop computer, personal computer, television, tablet, and the like. The alert may comprise any of a text message, an email, a notification, and the like.

At step 1055, the server 220 may update, based on the sensor data and whether the user followed the user recommendation output, the customized user output. For example, if the server 220 determines that the user has a high stress level, the server 220 may reduce the connected health output comprising the customized user output. A reduction in the connected health output may cause a reduction in the customized user output. If the server 220 determines that the user recommendation output to reduce stress was not implemented or completed, the server 220 may reduce the connected security output. For example, the server 220 may determine, based on the failure to implement or complete the user recommendation output, that the user is fairly risk prone. A reduction in the connected security output may lead to a reduction in the customized user output. If the user has a high stress level, but does implement or complete the user recommendation output in an attempt to relieve stress, the server 220 may leave the customized user output relatively unaffected (e.g., adjust the customized user output less than a predetermined value). For example, the server 220 may reduce the connected health output due to the stress, but the server 220 may increase the connected security output because the user took preventative measures to reduce stress based on the user recommendation output. The increase in the connected security output may balance out the decrease in the connected health output. Step 1055 may occur at any time throughout the method 1000. Furthermore, the method 1000 may be repeated whenever the server 220 receives additional sensor data regarding a user's stress level.

FIG. 11 shows a mobile device display in accordance with one or more aspects described herein. The display 1100 comprises an alert associated with a heavily populated calendar. Based on the calendar, and a description associated with each event on the calendar, the server 220 may determine that the user has a plurality of meetings throughout the afternoon. Additionally, the server 220 may determine, based on sensor data associated with a fitness tracker, that the user has an above average heart rate. Based on the determination that the user has a busy afternoon and a high heart rate, the server 220 may determine that the user is stressed about the meetings. As a result, the server 220 may prompt the user to listen to soothing music.

The server 220 may determine the alert based on the customized user output. For example, sensor data associated with the customized user output may reflect that the user typically has a busy work schedule. This may indicate a pattern of high stress associated with the user. The server 220 may also determine that the user is subject to high stress based on a single act, such as the spike in heart rate described above. If the user selects "Yes," the cell phone may begin streaming soothing music. The server 220 may indicate which music to play based on the customized user output. For example, sensor data associated with the customized user output may reflect that the user is a fan of jazz music. As a result, the cell phone may play jazz music. If the user selects "No thanks," the cell phone might not play the music. The selection of whether to follow the user recommendation output may impact the customized user output as discussed above with regard to step 1055.

Although FIG. 11 shows an alert comprising user recommendation output to reduce stress, the alert may comprise any type of user recommendation output, such as user recommendation output to take a yoga class, go exercise, avoid traffic, and the like. Furthermore, although FIG. 11 shows an alert comprising user recommendation output, the alert may also comprise an indication of a change in insurance rate, insurance promotions, promotions on additional products, or promotions on additional insurance products. Furthermore, although FIG. 11 shows the display 1100 of a mobile device, the alert may be displayed via a display comprising a different computing device, such as a laptop computer, personal computer, television, tablet, and the like. The alert may comprise any of a text message, an email, a notification, and the like.

Figure 12:
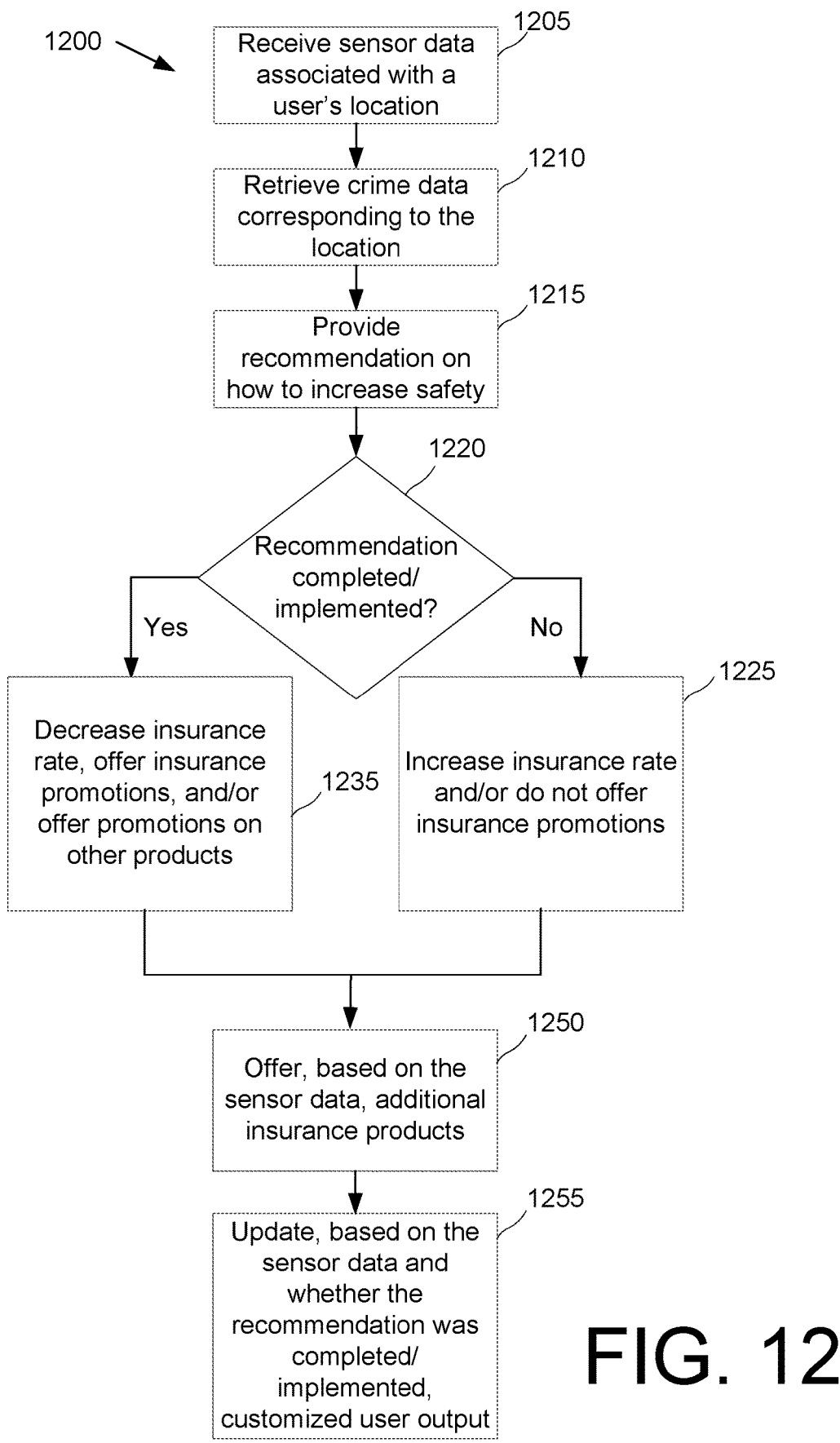
FIG. 12 shows a flow diagram for a method for determining benefits based on safety information associated with a given location in accordance with one or more aspects described herein.

FIG. 12 illustrates a flow diagram for a method 1200 for determining benefits based on safety information associated with a given location in accordance with one or more aspects described herein. The method 1200 or one or more steps thereof may be performed by one or more computing devices or entities. For example, portions of the method 1200 may be performed by components of the system 100 or the WAN networking environment 200. The method 1200 or one or more steps thereof may be embodied in computer-executable instructions that are stored in a computer-readable medium, such as a non-transitory computer readable medium. The steps in this flow diagram need not all be performed in the order specified and some steps may be omitted or changed in order. The method 1200 may be performed by a server, such as the server 220.

At step 1205, the server may receive sensor data associated with a user's location. For example, the sensor data may comprise at least one of GPS coordinates associated with the user's mobile device, information associated with recent credit card purchases at nearby vendors, or booking information such as a hotel or restaurant reservation.

At step 1210, the server 220 may retrieve crime data corresponding to the location. For example, the server 220 may cross reference the location against a crime database to determine how safe the location is. The server 220 may determine crime statistics of a precise location, crime statistics of the neighborhood/town/city/county associated with the precise location, and crime statistics of nearby neighborhoods/towns/cities/counties. For example, the server 220 may determine whether crime is prevalent in the area, when and where the last crime occurred, what types of crimes are typically committed, and the like.

At step 1215, based on the crime data and sensor data associated with the user, the server 220 may determine user recommendation output on how to increase the user's safety. The sensor data associated with the user may comprise products the user typically carries or personal characteristics associated with the user such as height, weight, age, or gender. The server 220 may transmit, to a computing device associated with the user, a message comprising the user recommendation output. For example, the user recommendation output may comprise an alert displayed on a user's cell phone. If the server 220 determines that the user is in an area associated with high crime statistics, the user recommendation output may suggest that the user be careful, be on the lookout for certain things, take a particular walking route, take transportation as opposed to walking, stay inside after dark, do not walk alone, do not use headphones while walking, do not use a cell phone while walking, and the like. The user recommendation output for the same location may vary from user to user based on the personal characteristics associated with each user. For example, a user recommendation output for a young child may be different from a user recommendation output for an adult.

At step 1220, the server 220 may determine whether the user recommendation output was completed or implemented. The server 220 may determine, based on sensor data associated with the user, whether the user recommendation output was completed or implemented. For example, the server 220 may determine that the user is currently walking, at night, through a neighborhood associated with high crime statistics. Based on this determination, the server 220 may suggest that the user take a particular route that is well lit. The server 220 may then receive GPS sensor data associated with the user that indicates that he or she took the suggested route.

In some examples, the user may provide an input via, for example, a cell phone indicating that he or she followed the user recommendation output. For example, the user recommendation output may comprise an alert suggesting that the user not walk alone around a given location. The server 220 might not be able to determine whether the user is alone, or with someone else. However, the alert may allow for a user input which may indicate whether the user recommendation output was implemented or completed. For example, the alert may comprise two buttons, "Thanks, will do," and "No thanks." The server 220 may receive a message of the user's selection, and may use the message to determine whether the user recommendation output was implemented. If the server 220 determines that the user recommendation output was not completed or implemented, the server 220 may proceed to step 1225. If the server 220 determines that the user recommendation output was completed or implemented, the server 220 may proceed to the step 1235. The server 202 may determine that although the user did not completely follow the user recommendation output, he or she exceeded a threshold for completing the user recommendation output. For example, the user recommendation output may comprise an indication that the user should follow a certain walking route through a particular neighborhood, and that the user should not wear headphones while walking. If the user follows the suggested route, keeps his or her headphones in, and mutes any music from playing, the server 220 may determine that although the user did not complete the user recommendation output, the user exceeded the implementation threshold.

At step 1225, the server 220 may transmit, to the user, an indication of an increased insurance rate. For example, by not following the user recommendation output, the user may indicate to the server 220 that he or she is a relatively high risk (e.g., level of risk exceeds a predetermined threshold) for an insurance company, and thus the insurance company may require higher premiums for coverage of the user. For example, the insurance company may increase the cost of home insurance, medical insurance, travel insurance, life insurance, and the like. The server 220 may also not offer insurance promotions to the user. For example, the insurance promotions may comprise an incentive for the user to follow the user recommendation output presented to the user. Thus, if the user fails to follow the user recommendation output, the user might not receive the incentive.

At step 1235, the server 220 may transmit, to the user, an indication of a decreased insurance rate. For example, by following the user recommendation output, the user may indicate to the server 220 that he or she is a relatively low risk (e.g., level of risk falls short of a predetermined threshold) for the insurance company. As a result, the insurance company may reward the user by reducing the cost of the user's coverage. For example, the insurance company may reduce the cost of home insurance, medical insurance, travel insurance, life insurance, and the like. The server 220 may transmit, to the user, an insurance promotion. The insurance promotion may comprise a reward for following the user recommendation output. For example, if the user is not currently insured, the server 220 may transmit the insurance promotion to incentivize the user to purchase insurance from the insurance company. The insurance promotion may be a promotion on home insurance, medical insurance, dental insurance, car insurance, boat insurance, travel insurance, life insurance, and the like. The server 220 may transmit, to the user, a promotion on other products. For example, the promotion on other products may comprise a reward for following the user recommendation output. The other products may be related to safety. For example, the other product may be a personal safety application for the user's mobile device. The other products may be determined based on sensor data comprising a customized user output associated with the user. The server 220 may determine the customized user output using the method 500 and/or the machine learning method described by the method 700. For example, sensor data comprising the customized user output may reflect that the user recently purchased an expensive home entertainment system. As a result, the server 220 may offer the user promotions on subscription video streaming services. The additional products may correspond to aspects of the customized user output. In some examples, the additional products might not correspond to a user's current customized user output, but may be offered to enrich the user's current experience. For example, the products may prompt the user to try something new. The customized user output may increase or decrease depending on how often the products are used.

At step 1250, the server 220 may transmit, to the user, an indication of additional insurance product. The server 220 may determine additional insurance products based on the sensor data. The server 220 may also determine the additional insurance products based on the customized user output. The sensor data may comprise a factor in determining the customized user output. For example, the sensor data may indicate that the user is currently in neighborhood associated with a high crime rate, and is walking alone at night. As a result of the high crime rate and the sensor data, the server may transmit an indication of an offer to purchase health/homeowners insurance to cover any personal or emotional injury and stolen property in the event that he or she is mugged while walking on the street. Based on information comprising the customized user output, the server 220 may determine that the user is walking through this neighborhood because he or she lives there, and that the user frequently makes this walk alone while coming home from work. The server 220 may also determine, based on information comprising the customized user output, the user recently purchased a motorcycle, which is kept outside of the house. The server 220 may transmit, to a computing device associated with the user, an offer for motorcycle insurance. Step 1250 may occur at any time throughout the method 1200.

At step 1255, the server 220 may update, based on the sensor data and based on whether the user recommendation output was completed or implemented, the customized user output. For example, if the user typically hangs around neighborhoods associated with a high crime rate, and the user recommendation output to take a certain walking route when walking alone at night is not completed or implemented, the server 220 may reduce the connected security output associated with the user. This may cause a decrease in the customized user output. If the user hangs around neighborhoods associated with a high crime rate, but the user recommendation output is completed or implemented, the server 220 may determine not to decrease the customized user output. Step 1255 may occur at any time throughout the method 1200. Furthermore, the method 1200 may be repeated whenever the server receives additional sensor data regarding a temporary residence.

Various aspects described herein may be embodied as a method, an apparatus, or as one or more computer-readable media storing computer-executable instructions. Accordingly, those aspects may take the form of an entirely hardware embodiment, an entirely software embodiment, or an embodiment combining software and hardware aspects. Any and/or all of the method steps described herein may be embodied in computer-executable instructions stored on a computer-readable medium, such as a non-transitory computer readable medium. Additionally or alternatively, any and/or all of the method steps described herein may be embodied in computer-readable instructions stored in the memory of an apparatus that includes one or more processors, such that the apparatus is caused to perform such method steps when the one or more processors execute the computer-readable instructions. In addition, various signals representing sensor or other data or events as described herein may be transferred between a source and a destination in the form of light and/or electromagnetic waves traveling through signal-conducting media such as metal wires, optical fibers, and/or wireless transmission media (e.g., air and/or space).

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the disclosure. Further, one or more aspects described with respect to one figure or arrangement may be used in conjunction with other aspects associated with another figure or portion of the description.

What is claimed is:

1. A method comprising:
   receiving, from a plurality of computing devices, sensor data associated with characteristics of a user;
   determining, based on a customized user output falling short of a predetermined threshold, a user recommendation output indicating one or more safety precautions corresponding to a neighborhood of the user, wherein the customized user output is a combination of connected outputs associated with one or more of the characteristics of the user;
   transmitting, to a user computing device of the plurality of computing devices associated with the user, the user recommendation output;
   determining, based on an indication received from at least one of the plurality of computing devices, completed performance of the user recommendation output; and
   transmitting, to the user computing device and based on the determining the completed performance of the user recommendation output, a second message comprising a positive benefit.

2. The method of claim 1, further comprising:
   determining, based on the sensor data and via one or more machine learning algorithms, the customized user output.

3. The method of claim 1, further comprising:
   determining whether the customized user output has already been generated for the user.

4. The method of claim 3, wherein the customized user output is generated in response to determining that the customized user output was not previously generated.

5. The method of claim 3, further comprising:
   updating, in response to determining that the customized user output was previously generated, the customized user output.

6. The method of claim 1, further comprising:
   determining, based on the customized user output, the positive benefit.

7. The method of claim 1, wherein the customized user output reflects a characteristic of the user, and wherein the positive benefit is determined based on the characteristic.

8. A system comprising:
   a processor; and
   a non-transitory memory storing computer-executable instructions thereon, wherein the computer-executable instructions, when executed by the processor, cause the processor to perform operations comprising:
      receiving, from a plurality of computing devices, sensor data associated with characteristics of a user;
      determining, based on a customized user output falling short of a predetermined threshold, a user recommendation output indicating one or more safety precautions corresponding to a neighborhood of the user, wherein the customized user output is a combination of connected outputs associated with one or more of the characteristics of the user;
      transmitting, to a user computing device of the plurality of computing devices associated with the user, the user recommendation output;
      determining, based on an indication received from at least one of the plurality of computing devices, completed performance of the user recommendation output; and
      transmitting, to the user computing device and based on the determining the completed performance of the first user recommendation output, a second message comprising a positive benefit.

9. The system of claim 8, wherein the computer-executable instructions, when executed by the processor, cause the processor to further perform operations comprising:
   determining, based on the sensor data and via one or more machine learning algorithms, the customized user output.

10. The system of claim 8, wherein the computer-executable instructions, when executed by the processor, cause the processor to further perform operations comprising:
    determining whether the customized user output has already been generated for the user.

11. The system of claim 10, wherein the customized user output is generated in response to determining that the customized user output was not previously generated.

12. The system of claim 10, wherein the computer-executable instructions, when executed by the processor, cause the processor to further perform operations comprising:
    updating, in response to determining that the customized user output was previously generated, the customized user output.

13. The system of claim 8, wherein the computer-executable instructions, when executed by the processor, cause the processor to further perform operations comprising:
    determining, based on the customized user output, the positive benefit.

14. The system of claim 8, wherein the customized user output reflects a characteristic of the user, and wherein the positive benefit is determined based on the characteristic.

15. A non-transitory computer-readable medium storing instructions thereon, wherein the instructions, when executed by a processor, cause the processor to perform operations comprising:
    receiving, from a plurality of computing devices, sensor data associated with characteristics of a user;
    determining, based on a customized user output falling short of a predetermined threshold, a user recommendation output indicating one or more safety precautions corresponding to a neighborhood of the user, wherein the customized user output is a combination of connected outputs associated with one or more of the characteristics of the user;
    transmitting, to a user computing device of the plurality of computing devices associated with the user, the user recommendation output;
    determining, based on an indication received from at least one of the plurality of computing devices, completed performance of the user recommendation output; and transmitting, to the user computing device and based on the determining the completed performance of the user recommendation output, a second message comprising a positive benefit.

16. The non-transitory computer-readable medium of claim 15, wherein the computer-executable instructions, when executed by the processor, cause the processor to further perform operations comprising:

determining, based on the sensor data and via one or more machine learning algorithms, the customized user output.

17. The non-transitory computer-readable medium of claim 15, wherein the computer-executable instructions, when executed by the processor, cause the processor to further perform operations comprising:

determining whether the customized user output has already been generated for the user.

18. The non-transitory computer-readable medium of claim 17, wherein the customized user output are generated in response to determining that the customized user output was not previously generated.

19. The non-transitory computer-readable medium of claim 17, wherein the computer-executable instructions, when executed by processor, cause the processor to further perform operations comprising:

updating, in response to determining that the customized user output was previously generated, the customized user output.

20. The non-transitory computer-readable medium of claim 15, wherein the computer-executable instructions, when executed by processor, cause the processor to further perform operations comprising:

determining, based on the customized user output, the positive benefit.

* * * * *